(12) United States Patent
Wurzer

(10) Patent No.: US 11,752,184 B2
(45) Date of Patent: *Sep. 12, 2023

(54) BIOACTIVE CONCENTRATES AND USES THEREOF

(71) Applicant: Purple Mundo, Inc., Santa Cruz, CA (US)

(72) Inventor: Joshua H. Wurzer, Boulder Creek, CA (US)

(73) Assignee: PURPLE MUNDO, INC., Santa Cruz, CA (US)

( * ) Notice: Subject to any disclaimer, the term of this patent is extended or adjusted under 35 U.S.C. 154(b) by 174 days.

This patent is subject to a terminal disclaimer.

(21) Appl. No.: 17/062,951

(22) Filed: Oct. 5, 2020

(65) Prior Publication Data

US 2021/0023156 A1  Jan. 28, 2021

Related U.S. Application Data

(63) Continuation of application No. 14/206,942, filed on Mar. 12, 2014, now Pat. No. 10,792,318.

(60) Provisional application No. 61/781,491, filed on Mar. 14, 2013, provisional application No. 61/781,479, filed on Mar. 14, 2013.

(51) Int. Cl.
*A61K 36/185* (2006.01)

(52) U.S. Cl.
CPC ........ *A61K 36/185* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 2009/0253783 A1 | 10/2009 | Goodwin et al. | |
| 2010/0239693 A1 | 9/2010 | Guy et al. | |
| 2010/0273895 A1 | 10/2010 | Stinchcomb et al. | |
| 2010/0292345 A1 | 11/2010 | Pertwee | |
| 2011/0028431 A1 | 2/2011 | Zerbe | |
| 2011/0318391 A1 | 12/2011 | Fuisz et al. | |
| 2012/0263804 A1 | 10/2012 | Hospodor | |
| 2013/0295172 A1 | 11/2013 | Freeman | |

FOREIGN PATENT DOCUMENTS

| | | |
|---|---|---|
| CA | 2424356 | 4/2003 |
| CA | 2489106 | 12/2003 |
| CA | 2792722 | 9/2011 |
| CN | 101253988 | 9/2008 |
| CN | 101317950 | 12/2008 |
| CN | 101317953 | 12/2008 |
| CN | 101524447 | 9/2009 |
| GB | 2400319 | 10/2004 |
| GB | 2417900 | 3/2006 |
| JP | 10194947 | 7/1998 |
| WO | 2008/024408 | 2/2008 |
| WO | 2012/144892 | 10/2012 |

OTHER PUBLICATIONS

Columbo et al., Comprehensive Medcinal Chemistry II, vol. 5, 2007, pp. 279-299.*
European Search Report, EP Application No. 14774471.8, dated Nov. 7, 2016, 7 pages.
N.N. "Hash Oil", Sep. 16, 2016, retrieved from the Internet: https://en.wikipedia.org/wiki/Hash_oil, 4 pages.
Casano et al., 7 pages, 2011.
Cannabinoids in Cannabis, The Canadian Consortium for the Investigation of Cannabinoids, 3 pages, 2009.

* cited by examiner

*Primary Examiner* — Michael V Meller
(74) *Attorney, Agent, or Firm* — Casimir Jones SC; John Mitchell Jones

(57) ABSTRACT

The present invention relates to concentrates obtained from extraction from *Cannabis*, preferably cannabinoid and/or terpene concentrates, and formulation of the concentrates, particularly for use for direct vaporization, infusion into edible matrices, in electronic inhalation devices, and as nutraceuticals.

17 Claims, No Drawings

BIOACTIVE CONCENTRATES AND USES THEREOF

CROSS-REFERENCE TO RELATED APPLICATIONS

This application is a continuation of U.S. patent application Ser. No. 14/206,942, filed Mar. 12, 2014, allowed as U.S. Pat. No. 10,792,318, which claims priority to U.S. Provisional Patent Application No. 61/781,491 filed Mar. 14, 2013 and to U.S. Provisional Patent Application No. 61/781,479 filed Mar. 14, 2013, the contents of each of which are incorporated by reference in their entirety.

FIELD OF THE INVENTION

The present invention relates to concentrates obtained from extraction from *Cannabis*, preferably cannabinoid and/or terpene concentrates, and formulation of the concentrates, particularly for use for direct vaporization, infusion into edible matrices, in electronic inhalation devices, and as nutraceuticals.

BACKGROUND OF THE INVENTION

Cannabinoids are a class of diverse chemical compounds that activate cannabinoid receptors. These include the endocannabinoids (produced naturally in the body by humans and animals), the phytocannabinoids (found in *Cannabis* and some other plants), and synthetic cannabinoids (produced chemically by humans). The most notable cannabinoid is the phytocannabinoid Δ9-tetrahydrocannabinol (THC), the primary psychoactive compound of *Cannabis*.

As mentioned, the main cannabinoid is $\Delta^9$-tetrahydrocannabinol (THC), which is recognized as the major psychoactive euphoriant responsible for the characteristic intoxication ('high') which follows the smoking or ingestion of *Cannabis*. High THC doses produce hallucinogenic effects. In addition to THC, several less potent metabolites and related compounds, such as the also psychoactive Δ 8-THC and cannabinol (CBN) are found in the *Cannabis* plant. Another major compound is cannabidiol (CBD), which has antagonistic effects to THC because it is a sedative compound. The ratio of THC to CBD in the plant is significant in terms of psychoactivity and is genetically determined.

A number of chemotypes exist within *Cannabis*. These are plants which are visually and botanically identical but which are chemically dissimilar. One type referred to as the fiber- or hemp-type contains predominantly CBD and only trace amounts of THC. Conversely, drug-type plants produce predominantly THC with trace quantities of CBD.

The issue is further complicated by the existence of an intermediate plant which contains approximately equal amounts of both THC and CBD. The concentrations of these and other cannabinoids vary enormously in practice depending on plant breeding and cultivation techniques and on post-harvest handling. THC is a highly unstable compound, breaking down in air and light to a number of inactive molecules, one of which, cannabinol (CBN), is commonly found in *Cannabis* products as they age. Other relatively abundant, and in certain rare chemotypes, predominant cannabinoids include cannabigerol (CBG), cannabichromene (CBC), tetrahydrocannabivarin (THCV), and cannabidivarin (CBDV) but in general little is known about the biological activities of these and the remaining less frequently occurring molecules.

Most pharmacological research has focused on THC and CBD. However, while THC is responsible for many of the effects of *Cannabis* drugs, it is important to bear in mind that THC and *Cannabis* are not synonymous for a number of reasons. Firstly, THC does not exist as such in the plant material but rather it is found as a carboxylic acid (THCA), as are other cannabinoids. While less studied, these carboxylic acid derivatives show pharmacological potential as well. These acids (THCA and CBDA) decompose slowly during storage to the corresponding chemically neutral but pharmacologically potent THC and CBD. This conversion is speeded up by the high temperatures involved in smoking and to a lesser extent by cooking or baking the drugs. Secondly, the THC/CBD ratio can markedly alter the effects of the drugs. Thirdly, some of the non-cannabinoid compounds from the plant may modulate the pharmacological effects of the cannabinoids. Terpenoids, which are responsible for the characteristic smell and flavor of *Cannabis*, have been postulated as influencing the effects yet experimental evidence is scarce. Some 1% by weight of the plant is composed of a mixture of 20 flavonoid compounds which are well known as antioxidants and which also scavenge damaging free radicals.

There has been considerable research regarding the first cannabinoid discovered in the *Cannabis* plant, cannabinol (CBN). While generally considered an unwanted degradation product of Δ9 Tetrahydrocannabinol (THC), CBN is a weak agonist of the CB1 and CB2 receptors. CBN is believed to cause drowsiness alone or when combined with CBD, THC, Cannagiberol (CBG), THCV, or Cannabichromene (CBC). As an isolated compound, CBN has shown moderate toxicity in animal models. Combined with other cannabinoids, THC, CBD, CBG, or CBC, it is believed that the toxicity is reduced due to the mediating effects of the other cannabinoids.

As can be seen, most research around active components of *Cannabis* has centered on THC and CBD. To this extract, there are many descriptions of processes making THC extracts and of products incorporating the extracts. However, there are relatively few reports of methods for extracting other bioactive compounds from *Cannabis* and the use of such bioactive extracts in a nutraceutical context. Accordingly, what is needed in the art are methods for producing and formulating bioactive extracts from *Cannabis* that contain desired compounds in addition to or other than THC.

SUMMARY OF THE INVENTION

The present invention relates to concentrates obtained from extraction from *Cannabis*, preferably cannabinoid and/or terpene concentrates, and formulation of the concentrates, particularly for use for direct vaporization, infusion into edible matrices, in electronic inhalation devices, and as nutraceuticals.

In some embodiments, the present invention provides processes for preparing cannabinoid and/or terpenoid extracts for human consumption comprising: (a) concentrating glandular trichomes from *Cannabis* plant material; (b) passing a solvent though the plant material to produce a cannabinoid/terpenoid-containing eluate; (c) filtering solids from the eluate; (d) refining the eluate to remove undesirable impurities; and (e) processing the eluate into a consumable form. In some embodiments, the refining comprises: (i) distilling the eluate; (ii) resuspending eluate in polar solvent; and (iii) cooling resuspended eluate to precipitate out undesirable impurities. In some embodiments, the refining comprises: (i) adding eluate to non-polar solvent; (ii) adding concentrated brine solution; (iii) agitating vigorously; (iv) draining off brine solution; and (v) treating the eluate with desiccant. In some embodiments, the methods further comprise the step of fractionating the eluate into fractions enriched for one or more cannabinoids and/or terpenoids. In some embodiments, the fractionating comprises passing the eluate over a column in the presence of solvents of progressively different polarities, and collecting fractions as they exit the column. In some embodiments, the fractionating comprises: (i) concentrating the eluate in a non-polar solvent; (ii) cooling the eluate solution to 20 to −200 C; and (iii) filtering crystals according to composition. In some embodiments, the refining comprises exposing eluate to UV light for at least 30 minutes to degrade chlorophyll. In some embodiments, the refining comprises: (i) adding solvent and activated charcoal to eluate; (ii) mixing; (iii) filtering out activated charcoal; and (iv) removing solvent. In some embodiments, processing the eluate into a consumable form comprises spray drying the eluate to produce a crystalline extract. In some embodiments, processing the eluate into a consumable form comprises thin film evaporation. In some embodiments, processing the eluate into a consumable form comprises continuously stirring the eluate with a whisk or auger until eluate is dried into a wax.

In some embodiments, the present invention provides a concentrate produced by the foregoing methods.

In some embodiments, the present invention provides a concentrate comprising at least 1% w/w of at least one cannabinoid compound selected from the group consisting of Cannabigerol (E)-CBG-C5, Cannabigerol monomethyl ether (E)-CBGM-C5 A, Cannabigerolic acid A (Z)-CBGA-C5 A, Cannabigerovarin (E)-CBGV-C3, Cannabigerolic acid A (E)-CBGA-C5 A, Cannabigerolic acid A monomethyl ether (E)-CBGAM-C5 A and Cannabigerovarinic acid A (E)-CBGVA-C3 A); (±)-Cannabichromene CBC-C5, (±)-Cannabichromenic acid A CBCA-C5 A, (±)-Cannabivarichromene, (±)-Cannabichromevarin CBCV-C3, (±)-Cannabichromevarinic acid A CBCVA-C3 A); (−)-Cannabidiol CBD-C5, Cannabidiol momomethyl ether CBDM-C5, Cannabidiol-C4 CBD-C4, (−)-Cannabidivarin CBDV-C3, Cannabidiorcol CBD-C1, Cannabidiolic acid CBDA-C5, Cannabidivarinic acid CBDVA-C3); Cannabinodiol CBND-C5, Cannabinodivarin CBND-C3); Δ9-Tetrahydrocannabinol Δ9-THC-C5, Δ9-Tetrahydrocannabinol-C4 Δ9-THC-C4, Δ9-Tetrahydrocannabivarin Δ9-THCV-C3, Δ9-Tetrahydrocannabiorcol, Δ9-THCO-C1, Δ9-Tetrahydrocannabinolic acid A Δ9-THCA-C5 A, Δ9-Tetrahydrocannabinolic acid B, Δ9-THCA-C5 B, Δ9-Tetrahydrocannabinolic acid-C4 A and/or B Δ9-THCA-C4 A and/or B, Δ9-Tetrahydro-cannabivarinic acid A Δ9-THCVA-C3 A, Δ9-Tetrahydrocannabiorcolic acid A and/or B Δ9-THCOA-C1 A and/or B), (−)-Δ8-trans-(6aR,10aR)-Δ8-Tetrahydrocannabinol Δ8-THC-C5, (−)-Δ8-trans-(6aR,10aR)-Tetrahydrocannabinolic acid A Δ8-THCA-C5 A, (−)-(6aS,10aR)-Δ9-Tetrahydrocannabinol (−)-cis-Δ9-THC-C5); Cannabinol CBN-C5, Cannabinol-C4 CBN-C4, Cannabivarin CBN-C3, Cannabinol-C2 CBN-C2, Cannabiorcol CBN-C1, Cannabinolic acid A CBNA-C5 A, Cannabinol methyl ether CBNM-C5, (−)-(9R,10R)-trans-Cannabitriol (−)-trans-CBT-C5, (+)-(9S,10S)-Cannabitriol (+)-trans-CBT-C5, (±)-(9R,10S/9S,10R)-); Cannabitriol (±)-cis-CBT-C5, (−)-(9R,10R)-trans-10-O-Ethyl-cannabitriol (−)-trans-CBT-OEt-C5, (±)-(9R,10R/9S,10S)-Cannabitriol-C3(±)-trans-CBT-C3, 8,9-Dihydroxy-Δ6a(10a)-tetrahydrocannabinol 8,9-Di-OH-CBT-C5, Cannabidiolic acid A cannabitriol ester CBDA-C5 9-OH-CBT-C5 ester, (−)-(6aR,9S,10S,10aR)-9,10-Dihydroxy-hexahydrocannabinol, Cannabiripsol, Cannabiripsol-C5, (−)-6a,7,10a-Trihydroxy-Δ9-tetrahydrocannabinol (−)-Cannabitetrol, 10-Oxo-Δ6a(10a)tetrahydrocannabinol OTHC); (5aS,6S,9R,9aR)-Cannabielsoin CBE-C5, (5aS,6S,9R,9aR)-C3-Cannabielsoin CBE-C3, (5aS,6S,9R,9aR)-Cannabielsoic acid A CBEA-C5 A, (5aS,6S,9R,9aR)-Cannabielsoic acid B CBEA-C5 B; (5aS,6S,9R,9aR)-C3-Cannabielsoic acid B CBEA-C3 B, Cannabiglendol-C3 OH-iso-HHCV-C3, Dehydrocannabifuran DCBF-C5, Cannabifuran CBF-C5), (−)-Δ7-trans-(1R,3R,6R)-Isotetrahydrocannabinol, (±)-Δ7-1,2-cis-(1R,3R,6S/1S,3S,6R)-Isotetrahydrocannabivarin, (−)-Δ7-trans-(1R,3R,6R)-Isotetrahydrocannabivarin); (±)-(1aS,3aR,8bR,8cR)-Cannabicyclol CBL-C5, (±)-(1aS,3aR,8bR,8cR)-Cannabicyclolic acid A CBLA-C5 A, (±)-(1aS,3aR,8bR,8cR)-Cannabicyclovarin CBLV-C3; Cannabicitran CBT-C5); Cannabichromanone CBCN-C5, Cannabichromanone-C3 CBCN-C3, and Cannabicoumaronone CBCON-C5); and at least 0.1% w/w of at least one terpenoid selected from the group consisting of Alloaromadendrene, allyl hexanoate, benzaldehyde, (Z)-α-cis-bergamotene, (Z)-α-trans-bergamotene, β-bisabolol, epi-α-bisabolol, β-bisabolene, borneol (camphol), cis-γ-bisabolene, borneol acetate (bornyl acetate), α-cadinene, camphene, camphor, cis-carveol, caryophyllene (β-caryophyllene), α-humulene (α-caryophyllene), γ-cadinene, Δ-β-carene, caryophyllene oxide, 1,8-cineole, citral A, citral B, cinnameldehyde, α-copaene (aglaiene), γ-curcumene, β-cymene, β-elemene, γ-elemene, ethyl decdienoate, ethyl maltol, ethyl propionate, ethylvanillin, eucalyptol, α-eudesmol, β-eudesmol, γ-eudesmol, eugenol, cis-β-farnesene ((Z)-β-farnesene), trans-α-farnesene, trans-β-farnesene, trans-γ bisabolene, fenchone, fenchol (norbornanol, β-fenchol), geraniol, α-guaiene, guaiol, methyl anthranilate, methyl salicylate, 2-methyl-4-heptanone, 3-methyl-4-heptanone, hexyl acetate, ipsdienol, isoamyl acetate, lemenol, limonene, d-limonene (limonene), linlool (linalyl alcohol, β-linolool), α-longipinene, menthol, γ-muurolene, myrcene (β-myrcene), nerolidol, trans-nerolidol, nerol, β-ocimene (cis-ocimene), octyl acetate, α-phellandrene, phytol, α-pinene (2-pinene), β-pinene, pulegone, sabinene, cis-sabinene hydrate (cis-thujanol), β-selinene, α-selinene, γ-terpinene, terpinolene (isoterpine), terpineol (α terpineol), terpineol-4-ol, α-terpinene (terpilene), α-thujene (origanene), vanillin, viridiflorene (ledene), and α-ylange.

In some embodiments, the concentrate comprises at least 1%, 2%, 5%, or 10% w/w of two or more of the cannabinoid compounds. In some embodiments, the concentrate comprises at least 1%, 2%, 5%, or 10% w/w of three or more of the cannabinoid compounds. In some embodiments, the concentrate comprises at least 1%, 2%, 5%, or 10% w/w of four or more of the cannabinoid compounds. In some embodiments, the concentrate comprises at least 1%, 2%, 5%, or 10% w/w of five of the cannabinoid compounds. In some embodiments, the concentrate comprises at least 0.01%, 0.05%, 0.1%, 0.5%, 1%, 2%, 3%, 4%, or 5% w/w of two or more of the terpenoids. In some embodiments, the concentrate comprises at least 0.01%, 0.05%, 0.1%, 0.5%, 1%, 2%, 3%, 4%, or 5% w/w of three or more of the terpenoids. In some embodiments, the concentrate comprises at least 0.01%, 0.05%, 0.1%, 0.5%, 1%, 2%, 3%, 4%, or 5% of four of the terpenoids. In some embodiments, the concentrate comprises at least 0.01%, 0.05%, 0.1%, 0.5%, 1%, 2%, 3%, 4%, or 5% w/w of five or more of the terpenoids. In some embodiments, the concentrate comprises at least 0.01%, 0.05%, 0.1%, 0.5%, 1%, 2%, 3%, 4%, or 5% w/w of ten or more of the terpenoids. In some embodiments, the concentrate is substantially free of THC-type compounds. In some embodiments, the concentrate is substantially free of CBN-type compounds.

In some embodiments, the concentrate comprise a total cannabinoid fraction of from about 45% to 98% w/w (calculated as a weight percentage of the total weight of the concentrate), most preferably about 65% to 95% w/w total cannabinoid compounds (e.g., as listed above) and a total terpenoid fraction of from about 0.1% to 5% w/w total terpenoids (e.g., as listed above; calculated as a weight percentage of the total weight of the concentrate). In some embodiments, the total cannabinoid fraction contains from about 62% to about 92% w/w or from about 75% to 92% w/w TCHA and THC combined (calculated as a weight percentage of the total weight of the concentrate). In other embodiments, the total cannabinoid fraction comprises from about 40% to 95% w/w or from about 60% to 92% w/w of a combination of CBG, CBC and THCV (calculated as a weight percentage of the total weight of the concentrate). As described above, the total cannabinoid fraction may additionally comprise at least 1%, 2%, 5%, or 10% w/w of three or more of the cannabinoid compounds (calculated as a weight percentage of the total weight of the concentrate). In some embodiments, the concentrate comprises at least 1%, 2%, 5%, or 10% w/w of four or more of the cannabinoid compounds (calculated as a weight percentage of the total weight of the concentrate). In some embodiments, the concentrate comprises at least 1%, 2%, 5%, or 10% w/w of five or more of the cannabinoid compounds. Likewise, the total terpenoid fraction may additionally comprise at least 0.01%, 0.05%, 0.1%, 0.2%, or 0.5% w/w of two or more of the terpenoids (calculated as a weight percentage of the total weight of the concentrate). In some embodiments, the total terpenoid fraction may additionally comprise at least 0.01%, 0.05%, 0.1%, 0.2° %, or 0.5% w/w of three or more of the terpenoids (calculated as a weight percentage of the total weight of the concentrate). In some embodiments, the total terpenoid fraction may additionally comprise at least 0.01%, 0.05%, 0.1%, 0.2%, or 0.5% w/w of four or more of the terpenoids (calculated as a weight percentage of the total weight of the concentrate). In some embodiments, the total terpenoid fraction may additionally comprise at least 0.01%, 0.05%, 0.1%, 0.2%, or 0.5% w/w of five or more of the terpenoids (calculated as a weight percentage of the total weight of the concentrate). In some embodiments, the total terpenoid fraction may additionally comprise at least 0.01%, 0.05%, 0.1%, 0.2%, or 0.5% w/w of ten or more of the terpenoids (calculated as a weight percentage of the total weight of the concentrate). It should be noted that in defining the concentrates in weight percentage terms, the weight percentage of the combined components will not exceed 100%.

In some embodiments, the present invention provides an oral delivery vehicle comprising a concentrate as described above.

In some embodiments, the present invention provides a chewing gum comprising a concentrate as described above.

In some embodiments, the present invention provides a dietary supplement as described above.

In some embodiments, the present invention provides a food product comprising a concentrate as described above.

In some embodiments, the present invention provides a thin film delivery vehicle comprising a concentrate as described above.

In some embodiments, the present invention provides a chewing gum composition comprising: (a) one or more cannabinoids, wherein the cannabinoids are present at less than 15% by weight; and (b) greater that 85% by weight gum base. In some embodiments, the gum further comprises a shell, wherein the shell encompasses the gum base. In some embodiments, the shell comprises cannabinoids. In some embodiments, the cannabinoids are complexed with an additional agent to enhance one or more of solubility or absorption. In some embodiments the cannabinoids are complexed with a cyclodexrin compound. In some embodiments, the one or more cannabinoids comprise a concentrate as provided above. In some embodiments, concentrate comprises one or more terpenoids as described above.

In some embodiments, the present invention provides a cannabinoid delivery system comprising one or more cannabinoid compounds embedded in a polymer-based thin film, wherein the polymer-based thin film is configured to dissolve upon contacting oral mucosa. In some embodiments, the cannabinoid compounds are complexed with a cyclodextrin compound. In some embodiments, a base polymer, comprising one or more of hydroxy propyl methyl cellulose, hydroxy propyl cellulose, starch, pullulan, pectin, and gelatin comprises at least 35% of the thin film. In some embodiments, the delivery systems further comprise one or more additional components alter the mucoadhesion, flexibility, or rate of dissolving of the thin film. In some embodiments, the one or more cannabinoids comprise a concentrate as provided above. In some embodiments, concentrate comprises one or more terpenoids as described above.

In some embodiments, the present invention provides methods of rapidly delivering a dose of cannabinoid to the bloodstream of a subject comprising: (a) placing a cannabinoid delivery system as described above on the oral mucosa of the subject; and (b) allowing the thin film of the delivery system to dissolve, thereby releasing a dose on cannabinoid onto the oral mucosa. In some embodiments, the dose comprises 2-200 mg of cannabinoid.

In some embodiments, the present invention provides for use of a concentrate, cannabinoid delivery system, oral delivery vehicle, topical skin care product, dietary supplement, chewing gum or food product as described above to reduce inflammation, reduce pain, reduce nausea, enhance mood, produce a calm feeling, induce drowsiness or sleep, reduce anxiety, support joint health, support mental health, support anti-inflammatory response by the body, support brain function, support feelings of wellbeing, support healthy skin and reduce blemishes.

In some embodiments, the present invention provides methods of reducing inflammation, reducing pain, reducing nausea, enhancing mood, producing a calm feeling, inducing drowsiness or sleep, reducing anxiety, supporting joint health, supporting mental health, supporting anti-inflammatory response by the body, support braining function, supporting feelings of wellbeing, supporting healthy skin or reduce blemishes in a subject comprising administering an effective amount of a concentrate, cannabinoid delivery system, oral delivery vehicle, dietary supplement, chewing gum or food product as described above.

The present invention further relates to extracts concentrates obtained from extraction from *cannabis*, preferably cannabinoid and/or terpene concentrates, wherein THC is converted to one or more natural CBN-type cannabinoids by an oxidizing treatment. The extracts and concentrates find use for direct vaporization, infusion into edible matrices, infusion into topical skin care products, in electronic inhalation devices, and as nutraceuticals. The present invention relates to extracts concentrates obtained from extraction from *cannabis*, preferably cannabinoid and/or terpene concentrates, wherein THC is converted to one or more natural CBN-type cannabinoids by an oxidizing treatment. The extracts and concentrates find use for direct vaporization, infusion into edible matrices, in electronic inhalation devices, and as nutraceuticals.

In some embodiments, the present invention provides methods of converting THC in a THC extract to CBN comprising: (a) contacting the THC extract with an oxidizing agent under conditions such that THC is oxidized to CBN; and (b) allowing sufficient time for the oxidizing agent to react with the THC extract such that THC is converted to one or more CBN-type cannabinoids to provide a converted-CBN extract. In some embodiments, the THC is in an organic solvent. In some embodiments, the methods further comprise a step between steps (a) and (b) of decarboxylating THC(a) present in the THC-rich extract to yield additional THC. In some embodiments, step (c) is performed under exposure to UV light and in the presence of an oxygen source. In some embodiments, the oxidizing agent is selected from the group consisting of hydrogen peroxide, ozone, halogens, sulfuric acid, peroxydisulfuric acid, permamnganate compounds, and nitrous oxide. In some embodiments, from about 10 to about 95% of THC in the THC extract is converted to a CBN-type cannabinoid.

In some embodiments, the THC extract is a THC concentrate. In some embodiments, the THC concentrate is prepared by: (a) concentrating glandular trichomes from *cannabis* plant material; (b) passing a solvent though the plant material to produce a cannabinoid/terpenoid-containing eluate; (c) filtering solids from the eluate; and (d) refining the eluate to remove undesirable impurities.

In some embodiments, the THC extract is co-enriched for one or more terpenoids. In some embodiments, the one or more terpenoids are selected from the group consisting of Alloaromadendrene, allyl hexanoate, benzaldehyde, (Z)-α-cis-bergamotene, (Z)-α-trans-bergamotene, β-bisabolol, epi-α-bisabolol, β-bisabolene, borneol (camphol), cis-γ-bisabolene, borneol acetate (bornyl acetate), α-cadinene, camphene, camphor, cis-carveol, caryophyllene (β-caryophyllene), α-humulene (α-caryophyllene), γ-cadinene, Δ-3-carene, caryophyllene oxide, 1,8-cineole, citral A, citral B, cinnameldehyde, α-copaene (aglaiene), γ-curcumene, β-cymene, β-elemene, γ-elemene, ethyl decdienoate, ethyl maltol, ethyl propionate, ethylvanillin, eucalyptol, α-eudesmol, β-eudesmol, γ-eudesmol, eugenol, cis-β-farnesene ((Z)-β-farnesene), trans-α-farnesene, trans-β-farnesene, trans-γ bisabolene, fenchone, fenchol (norbornanol, β-fenchol), geraniol, α-guaiene, guaiol, methyl anthranilate, methyl salicylate, 2-methyl-4-heptanone, 3-methyl-4-heptanone, hexyl acetate, ipsdienol, isoamyl acetate, lemenol, limonene, d-limonene (limonene), linlool (linalyl alcohol, β-linolool), α-longipinene, menthol, γ-muurolene, myrcene (β-myrcene), nerolidol, trans-nerolidol, nerol, β-ocimene (cis-ocimene), octyl acetate, α-phellandrene, phytol, α-pinene (2-pinene), β-pinene, pulegone, sabinene, cis-sabinene hydrate (cis-thujanol), β-selinene, α-selinene, γ-terpinene, terpinolene (isoterpine), terpineol (a terpineol), terpineol-4-ol, α-terpinene (terpilene), α-thujene (origanene), vanillin, viridiflorene (ledene), α-ylangene.

In some embodiments, the methods further comprise the step of formulating the CBN-converted extract with a nutraceutically or pharmaceutically acceptable carrier. In some embodiments, the methods further comprise combining the CBN-converted extract with one or more bioactive agents, nutraceutical agents, or phytonutrients. In some embodiments, the one or more bioactive agents, nutraceutical agents, or phytonutrients is from a source other than *cannabis*. In some embodiments, the methods further comprise incorporating the CBN-converted extract into an oral delivery vehicle selected from the group consisting of a tablet, capsule, chewable matrix, dissolvable film, and chewing gum. In some embodiments, the methods further comprise incorporating the CBN-converted extract into a vaporizable formulation.

In some embodiments, the present invention provides a converted-CBN concentrate produced by the processes described above.

In some embodiments, the present invention provides a converted CBN-concentrate comprising at least 20% of one or more CBN-type cannabinoids selected from the group consisting of Cannabinol CBN-C5, Cannabinol-C4 CBN-C4, Cannabivarin CBN-C3, Cannabinol-C2 CBN-C2, Cannabiorcol CBN-C1, Cannabinolic acid A CBNA-C5 A, and Cannabinol methyl ether CBNM-C5. In some embodiments, the concentrate comprises at least 30% of one or more CBN-type cannabinoids selected from the group consisting of Cannabinol CBN-C5, Cannabinol-C4 CBN-C4, Cannabivarin CBN-C3, Cannabinol-C2 CBN-C2, Cannabiorcol CBN-C1, Cannabinolic acid A CBNA-C5 A, and Cannabinol methyl ether CBNM-C5. In some embodiments, the concentrate comprises at least 50% of one or more CBN-type cannabinoids selected from the group consisting of Cannabinol CBN-C5, Cannabinol-C4 CBN-C4, Cannabivarin CBN-C3, Cannabinol-C2 CBN-C2, Cannabiorcol CBN-C1, Cannabinolic acid A CBNA-C5 A, and Cannabinol methyl ether CBNM-C5. In some embodiments, the concentrate comprises at least 70% of one or more CBN-type cannabinoids selected from the group consisting of Cannabinol CBN-C5, Cannabinol-C4 CBN-C4, Cannabivarin CBN-C3, Cannabinol-C2 CBN-C2, Cannabiorcol CBN-C1, Cannabinolic acid A CBNA-C5 A, and Cannabinol methyl ether CBNM-C5. In some embodiments, the concentrate comprises at least 90% of one or more CBN-type cannabinoids selected from the group consisting of Cannabinol CBN-C5, Cannabinol-C4 CBN-C4, Cannabivarin CBN-C3, Cannabinol-C2 CBN-C2, Cannabiorcol CBN-C1, Cannabinolic acid A CBNA-C5 A, and Cannabinol methyl ether CBNM-C5.

In some embodiments, the concentrate further comprises at least 1% of at least a second cannabinoid selected from the group consisting of Cannabigerol (E)-CBG-C5, Cannabigerol monomethyl ether (E)-CBGM-C5 A, Cannabigerolic acid A (Z)-CBGA-C5 A, Cannabigerovarin (E)-CBGV-C3, Cannabigerolic acid A (E)-CBGA-C5 A, Cannabigerolic acid A monomethyl ether (E)-CBGAM-C5 A and Cannabigerovarinic acid A (E)-CBGVA-C3 A); (±)-Cannabichromene CBC-C5, (±)-Cannabichromenic acid A CBCA-C5 A, (±)-Cannabivarichromene, (±)-Cannabichromevarin CBCV-C3, (±)-Cannabichromevarinic acid A CBCVA-C3 A); (−)-Cannabidiol CBD-C5, Cannabidiol momomethyl ether CBDM-C5, Cannabidiol-C4 CBD-C4, (−)-Cannabidivarin CBDV-C3, Cannabidiorcol CBD-C1, Cannabidiolic acid CBDA-C5, Cannabidivarinic acid CBDVA-C3); Cannabinodiol CBND-C5, Cannabinodivarin CBND-C3), (−)-(9R,10R)-trans-Cannabitriol (−)-trans-CBT-C5, (+)-(9S,10S)-Cannabitriol (+)-trans-CBT-C5, (±)-(9R,10S/9S,10R)-); Cannabitriol (±)-cis-CBT-C5, (−)-(9R,10R)-trans-10-O-Ethyl-cannabitriol (−)-trans-CBT-OEt-C5, (±)-(9R,10R/9S,10S)-Cannabitriol-C3(±)-trans-CBT-C3, 8,9-Dihydroxy-Δ6a(10a)-tetrahydrocannabinol 8,9-Di-OH-CBT-C5, Cannabidiolic acid A cannabitriol ester CBDA-C5 9-OH-CBT-C5 ester, (−)-(6aR,9S,10S,10aR)-9,10-Dihydroxy-hexahydrocannabinol, Cannabiripsol, Cannabiripsol-C5, (−)-6a,7,10a-Trihydroxy-Δ9-tetrahydrocannabinol (−)-Cannabitetrol, 10-Oxo-Δ6a(10a)tetrahydrocannabinol OTHC); (5aS,6S,9R,9aR)-Cannabielsoin CBE-C5, (5aS,6S,9R,9aR)-C3-Cannabielsoin CBE-C3, (5aS,6S,9R,9aR)-Cannabielsoic acid A CBEA-C5 A, (5aS,6S,9R,9aR)-Cannabielsoic acid B CBEA-C5 B; (5aS,6S,9R,9aR)-C3-Cannabielsoic acid B CBEA-C3 B, Cannabiglendol-C3 OH-iso-HHCV-C3, Dehydrocannabifuran DCBF-C5, Cannabifuran CBF-C5), (−)-Δ7-trans-(1R,3R,6R)-Isotetrahydrocannabinol, (±)-Δ7-1,2-cis-(1R,3R,6S/1S,3S,6R)-Isotetrahydrocannabivarin, (−)-Δ7-trans-(1R,3R,6R)-Isotetrahydrocannabivarin); (±)-(1 aS,3aR,8bR,8cR)-Cannabicyclol CBL-C5, (±)-(1aS,3aR,8bR,8cR)-Cannabicyclolic acid A CBLA-C5 A, (±)-(1aS,3aR,8bR,8cR)-Cannabicyclovarin CBLV-C3; Cannabicitran CBT-C5); Cannabichromanone CBCN-C5, Cannabichromanone-C3 CBCN-C3, and Cannabicoumaronone CBCON-C5). In some embodiments, the concentrate comprises at least 1% w/w of two of the cannabinoid compounds. In some embodiments, the concentrate comprises at least 1% w/w of three of the cannabinoid compounds. In some embodiments, the concentrate comprises at least 1% w/w of four of the cannabinoid compounds. In some embodiments, the concentrate comprises at least 1% w/w of five of the cannabinoid compounds.

In some embodiments, the concentrate is further co-enriched for at least 0.1% w/w of at least one terpenoid selected from the group consisting of Alloaromadendrene, allyl hexanoate, benzaldehyde, (Z)-α-cis-bergamotene, (Z)-α-trans-bergamotene, β-bisabolol, epi-α-bisabolol, β-bisabolene, borneol (camphol), cis-γ-bisabolene, borneol acetate (bornyl acetate), α-cadinene, camphene, camphor, cis-carveol, caryophyllene (β-caryophyllene), α-humulene (α-caryophyllene), γ-cadinene, Δ-3-carene, caryophyllene oxide, 1,8-cineole, citral A, citral B, cinnameldehyde, α-copaene (aglaiene), γ-curcumene, β-cymene, β-elemene, γ-elemene, ethyl decdienoate, ethyl maltol, ethyl propionate, ethylvanillin, eucalyptol, α-eudesmol, β-eudesmol, γ-eudesmol, eugenol, cis-β-farnesene ((Z)-β-farnesene), trans-α-farnesene, trans-β-farnesene, trans-γ bisabolene, fenchone, fenchol (norbornanol, β-fenchol), geraniol, α-guaiene, guaiol, methyl anthranilate, methyl salicylate, 2-methyl-4-heptanone, 3-methyl-4-heptanone, hexyl acetate, ipsdienol, isoamyl acetate, lemenol, limonene, d-limonene (limonene), linolool (linalyl alcohol, β-linolool), α-longipinene, menthol, γ-muurolene, myrcene (β-myrcene), nerolidol, trans-nerolidol, nerol, β-ocimene (cis-ocimene), octyl acetate, α-phellandrene, phytol, α-pinene (2-pinene), β-pinene, pulegone, sabinene, cis-sabinene hydrate (cis-thujanol), β-selinene, α-selinene, γ-terpinene, terpinolene (isoterpine), terpineol (α terpineol), terpineol-4-ol, α-terpinene (terpilene), α-thujene (origanene), vanillin, viridiflorene (ledene), α-ylangene. In some embodiments, the concentrate comprises at least 0.1% of two of the terpenoids. In some embodiments, the concentrate comprises at least 0.1% of three of the terpenoids. In some embodiments, the concentrate comprises at least 0.1% of four of the terpenoids. In some embodiments, the concentrate comprises at least 0.1% of five of the terpenoids.

In some embodiments, the concentrates comprise a total cannabinoid fraction of from about 45% to 98% w/w (calculated as a weight percentage of the total weight of the concentrate), most preferably about 65% to 95% w/w total CBN-type compounds (e.g., as listed above) and a total terpenoid fraction of from about 0.1% to 5% w/w total terpenoids (e.g., as listed above; calculated as a weight percentage of the total weight of the concentrate). In some embodiments, the total cannabinoid fraction contains from about 62% to about 92% w/w or from about 75% to 92% w/w CBN-type compounds (calculated as a weight percentage of the total weight of the concentrate). As described above, the total cannabinoid fraction may additionally comprise at least 1%, 2%, 5%, or 10% w/w of three or more of the cannabinoid compounds (calculated as a weight percentage of the total weight of the concentrate). In some embodiments, the concentrate comprises at least 1%, 2%, 5%, or 10% w/w of four or more of the cannabinoid compounds (calculated as a weight percentage of the total weight of the concentrate). In some embodiments, the concentrate comprises at least 1%, 2%, 5%, or 10% w/w of five or more of the cannabinoid compounds. Likewise, the total terpenoid fraction may additionally comprise at least 0.01%, 0.05%, 0.1%, 0.2%, or 0.5% w/w of two or more of the terpenoids (calculated as a weight percentage of the total weight of the concentrate). In some embodiments, the total terpenoid fraction may additionally comprise at least 0.01%, 0.05%, 0.1%, 0.2%, or 0.5% w/w of three or more of the terpenoids (calculated as a weight percentage of the total weight of the concentrate). In some embodiments, the total terpenoid fraction may additionally comprise at least 0.01%, 0.05%, 0.1%, 0.2%, or 0.5% w/w of four or more of the terpenoids (calculated as a weight percentage of the total weight of the concentrate). In some embodiments, the total terpenoid fraction may additionally comprise at least 0.01%, 0.05%, 0.1%, 0.2%, or 0.5% w/w of five or more of the terpenoids (calculated as a weight percentage of the total weight of the concentrate). In some embodiments, the total terpenoid fraction may additionally comprise at least 0.01%, 0.05%, 0.1%, 0.2%, or 0.5% w/w of ten or more of the terpenoids (calculated as a weight percentage of the total weight of the concentrate). It should be noted that in defining the concentrates in weight percentage terms, the weight percentage of the combined components will not exceed 100%. It should be noted that in defining the concentrates in weight percentage terms, the weight percentage of the combined components will not exceed 100%.

In some embodiments, the concentrate is substantially free of THC-type compounds.

In some embodiments, the present invention provides an oral delivery vehicle comprising a concentrate as described above.

In some embodiments, the present invention provides a chewing gum comprising a concentrate as described above.

In some embodiments, the present invention provides an oral delivery vehicle comprising a concentrate as described above.

In some embodiments, the present invention provides a dietary supplement comprising a concentrate as described above.

In some embodiments, the present invention provides a food product comprising a concentrate as described above.

In some embodiments, the present invention provides a thin film delivery vehicle comprising a concentrate as described above.

In some embodiments, the present invention provides a composition comprising a concentrate as described in combination with one or more bioactive agents, nutraceutical agents, phytonutrients, or pharmaceutically acceptable carriers and combinations thereof.

In some embodiments, the present invention provides for use of a concentrate, cannabinoid delivery system, oral delivery vehicle, dietary supplement, chewing gum, food product or composition as described above to ameliorate the psychoactive responses produced by other cannabinoids, reduce inflammation, reduce pain, reduce pain associated with cancer, reduce neuropathic pain, reduce nausea, enhance mood, produce a calm feeling, induce drowsiness or sleep, reduce anxiety, support joint health, support mental health, support anti-inflammatory response by the body, support brain function, support feelings of wellbeing, support healthy skin and reduce blemishes.

In some embodiments, the present invention provides methods of ameliorating psychoactive responses produced by other cannabinoids, reducing inflammation, reducing pain, reducing nausea, enhancing mood, producing a calm feeling, inducing drowsiness or sleep, reducing anxiety, supporting joint health, supporting mental health, supporting anti-inflammatory response by the body, supporting brain function, supporting feelings of wellbeing, supporting healthy skin or reducing blemishes in a subject comprising administering an effective amount of a concentrate, cannabinoid delivery system, oral delivery vehicle, dietary supplement, chewing gum or food product as described above.

Definitions

As used herein the term "*Cannabis*" is used to refer to plants of the genus *Cannabis*, including *Cannabis sativa*, *Cannabis indica*, and *Cannabis ruderalis*.

As used herein, the terms "trichome" and "glandular trichome" are used interchangeably to refer to plant epidermal structures that comprise secretions produced by the plant.

As used herein, the term "cannabinoid" refers to a chemical compound that shows direct or indirect activity at a cannabinoid receptor. There are two main cannabinoid receptors, $CB_1$ and $CB_2$. Other receptors that research suggests have cannabinoid activity include the GPR55 and GPR 18 receptors. The term "phytocannabinoid" refers to cannabinoids that occur in a plant species or are derived from cannabinoids occurring in a plant species. Examples of cannabinoids include, but are not limited to, Tetrahydrocannabinol (THC), Cannabidiol (CBD), Cannabinol (CBN), Cannabigerol (CBG), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol Monomethyl Ether (CBGM). Examples of structures of cannabinoids include, but are not limited to:

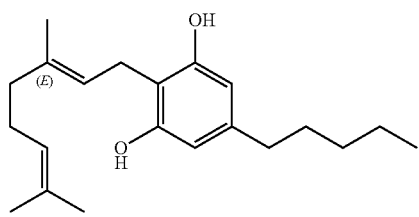

Cannabigerol

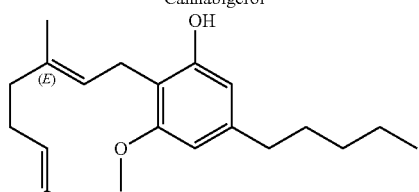

Cannabigerol monomethyl ether

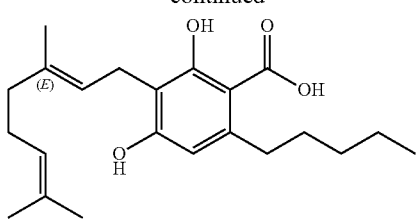

Cannabigerolic acid A

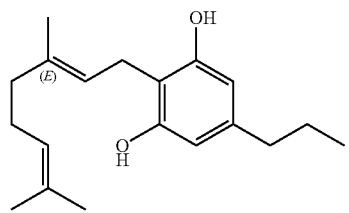

Cannabigerovarin

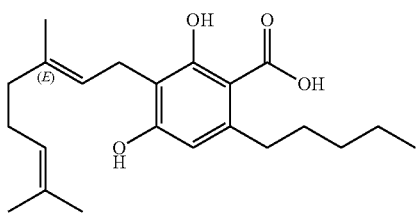

Cannabigerolic acid A
(E)-CBGA-C<sub>5</sub> A

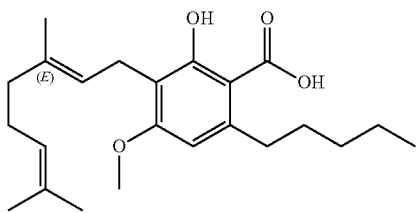

Cannabigerolic acid A
monomethyl ether
(E)-CBGAM-C<sub>5</sub> A

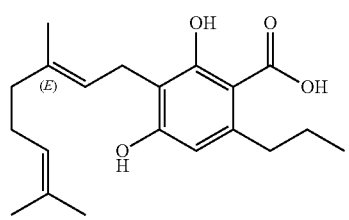

Cannabigerovarinic acid A
(E)-CBGVA-C<sub>3</sub> A

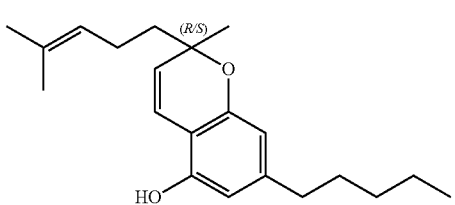

(±)-Cannabichromene
CBC-C<sub>5</sub>

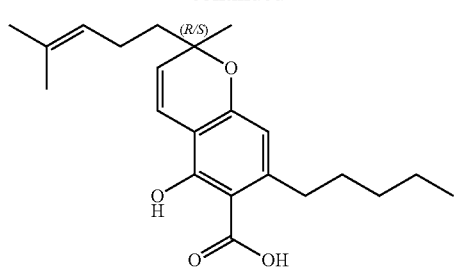
(±)-Cannabichromenic acid A
CBCA-C₅ A
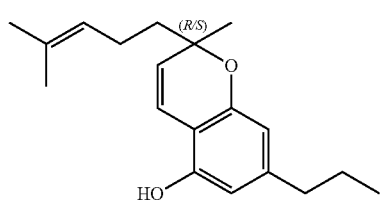
(±)-Cannabivarichromene,
(±)-Cannabichromevarin
CBCV-C₃
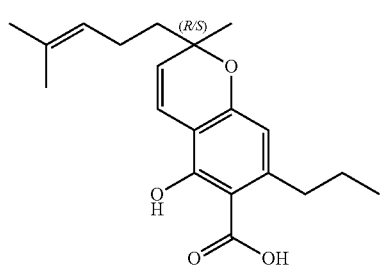
(±)-Cannabichromevarinic
acid A
CBCVA-C₃ A
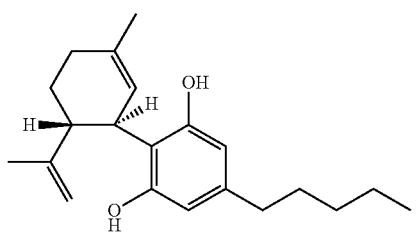
(-)-Cannabidiol
CBD-C₅
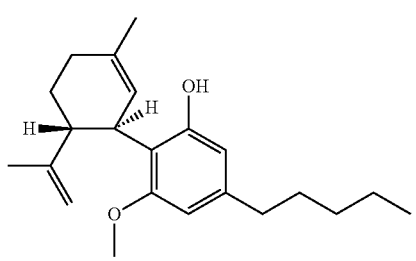
Cannabidiol
monomethyl ether
CBDM-C₅
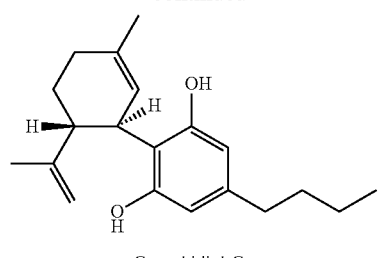
Cannabidiol-C₄
CBD-C₄
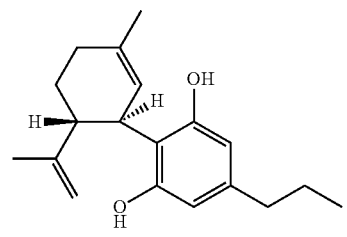
(-)-Cannabidivarin
CBDV-C₃
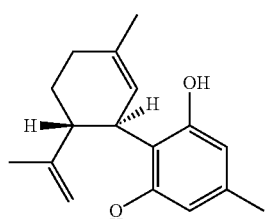
Cannabidiorcol
CBD-C₁
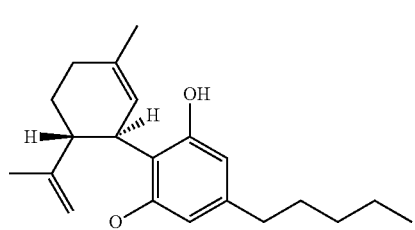
Cannabidiolic acid
CBDA-C₅
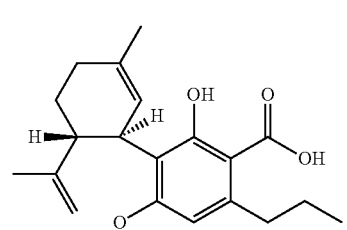
Cannabidivarinic acid
CBDVA-C₃

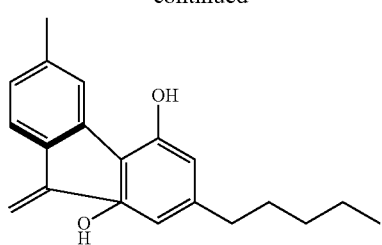

Cannabinodiol
CBND-C$_5$

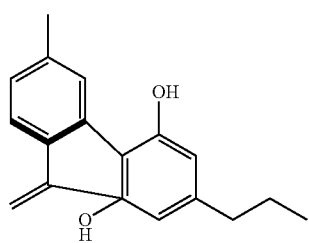

Cannabinodivarin
CBND-C$_3$

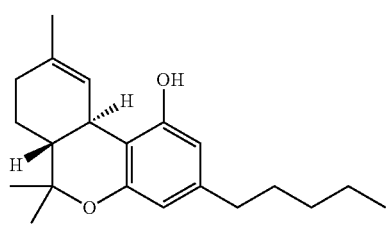

$\Delta^9$-Tetrahydrocannabinol
$\Delta^9$-THC-C$_5$

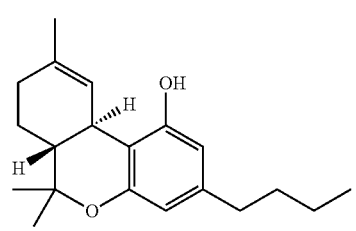

$\Delta^9$-Tetrahydrocannabinol-C$_4$
$\Delta^9$-THC-C$_4$

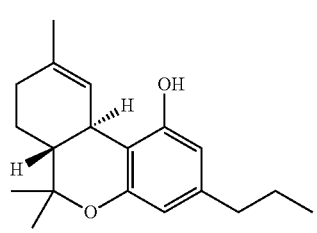

$\Delta^9$-Tetrahydrocannabivarin
$\Delta^9$-THCV-C$_3$

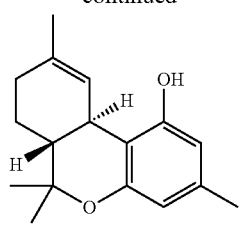

$\Delta^9$-Tetrahydrocannabiorcol
$\Delta^9$-THCO-C$_1$

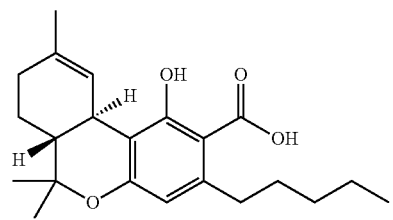

$\Delta^9$-Tetrahydro-cannabinolic acid A
$\Delta^9$-THCA-C$_5$ A

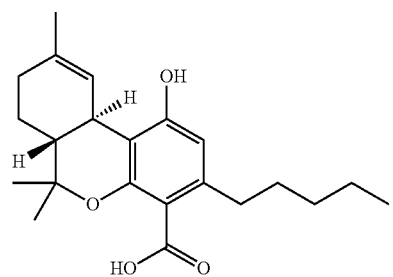

$\Delta^9$-Tetrahydro-cannabinolic acid B
$\Delta^9$-THCA-C$_5$ B

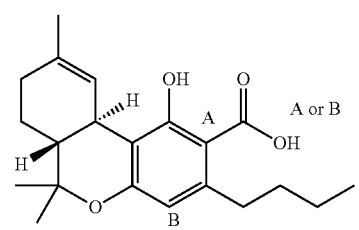

$\Delta^9$-Tetrahydro-cannabinolic acid-C$_4$
A and/or B
$\Delta^9$-THCA-C$_4$ A and/or B

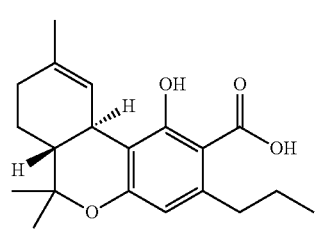

$\Delta^9$-Tetrahydro-cannabivarinic acid A
$\Delta^9$-THCA-C$_3$ A

-continued

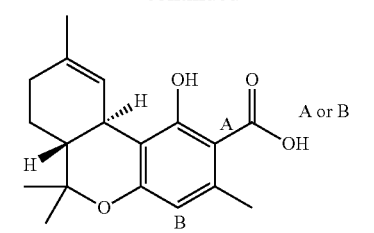

Δ⁹-Tetrahydro-cannabiorcolic acid
A and/or B
Δ⁹-THCOA-C₁ A and/or B

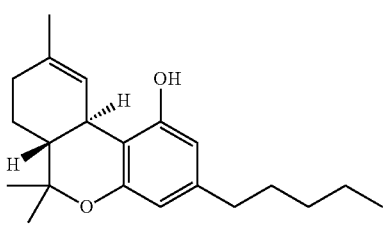

(−)-Δ⁸-trans-(6aR,10aR)-
Δ⁸-Tetrahydrocannabinol
Δ⁸-THC-C₅

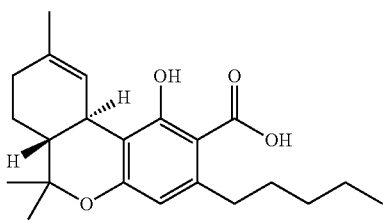

(−)-Δ⁸-trans-(6aR,10aR)-
Tetrahydrocannabinolic
acid A
Δ⁸-THCA-C₅ A

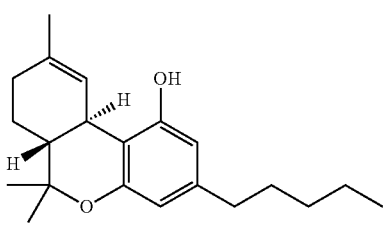

(−)-(6aS,10aR)-Δ⁹-
Tetrahydrocannabinol
(−)-cis-Δ⁹-THC-C₅

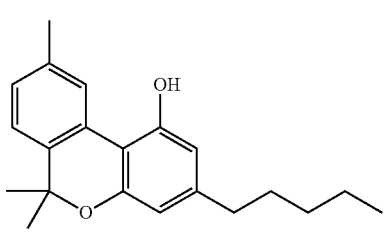

Cannabinol
CBN-C₅

-continued

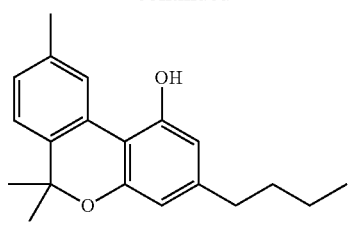

Cannabinol-C₄
CBN-C₄

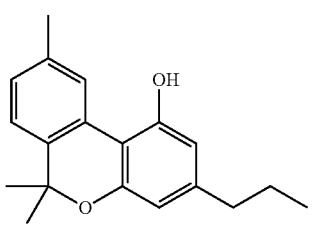

Cannabivarin
CBN-C₃

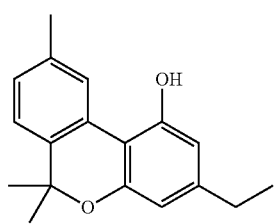

Cannabinol-C₂
CBN-C₂

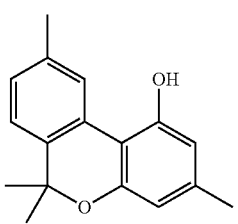

Cannabiorcol
CBN-C₁

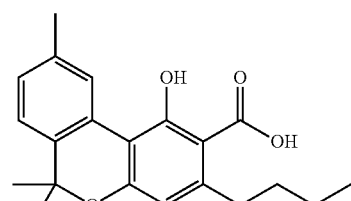

Cannabinolic acid A
CBNA-C₅ A

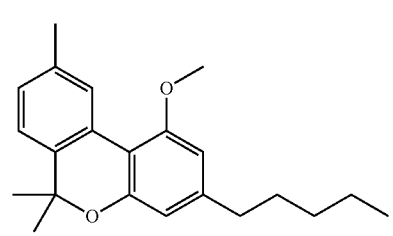

Cannabinolic methyl ether
CBNM-C₅

-continued

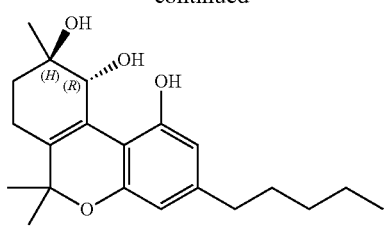

(−)-(9R,10R)-trans-
Cannabitriol
(−)-trans-CBT-C$_5$

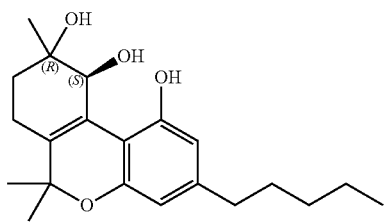

(+)-(9S,10S)-Cannabitriol
(+)-trans-CBT-C$_5$

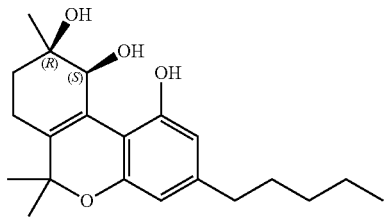

(±)-(9R,10S/9S,10R)-
Cannabitriol
(±)-cis-CBT-C$_5$

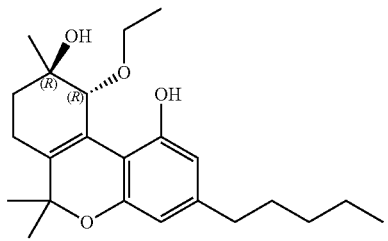

(−)-(9R,10R)-trans-
10-O-Ethyl-cannabitriol
(−)-trans-CBT-OEt-C$_5$

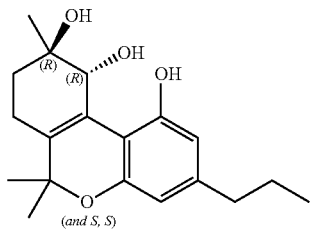

(±)-(9R,10R/9S,10S)-
Cannabitriol-C$_3$
(±)-trans-CBT-C$_3$

-continued

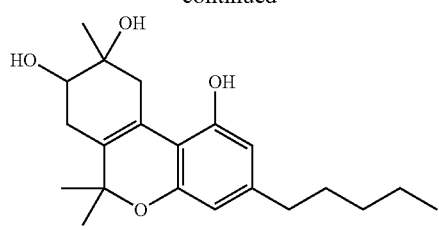

8,9-Dihydroxy-Δ$^{6a(10a)}$-
tetrahydrocannabinol
8,9-Di-OH-CBT-C$_5$

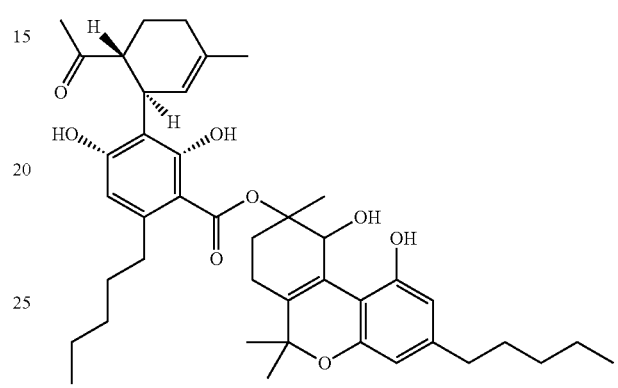

Cannabidiolic acid A
cannabitriol ester
CBDA-C$_5$ 9-OH-CBT-C$_5$ ester

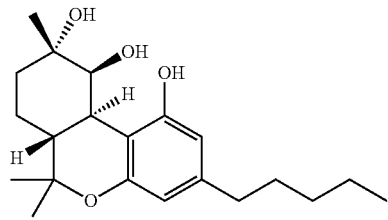

(−)-(6aR,9S,10S,10aR)-
9,10-Dihydroxy-
hexahydrocannabinol,
Cannabiripsol
Cannabiripsol-C$_5$

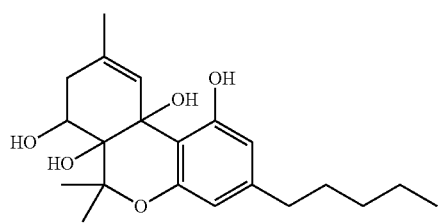

(−)-6a,7,10a-Trihydroxy-
Δ$^9$-tetrahydrocannabinol
(−)-Cannabitetrol

-continued

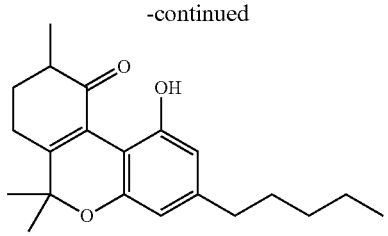

10-Oxo-Δ$^{6a(10a)}$-
tetrahydrocannabinol
OTHC

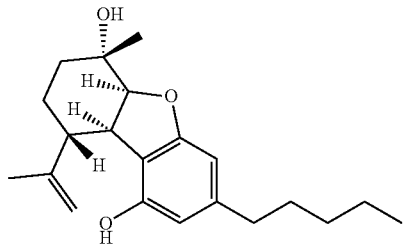

(5aS,6S,9R,9aR)-
Cannabielsoin
CBE-C$_5$

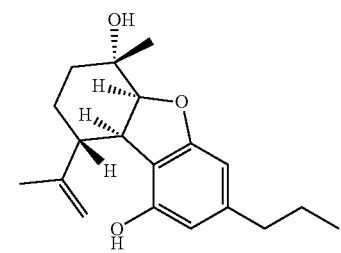

(5aS,6S,9R,9aR)-
C$_3$-Cannabielsoin
CBE-C$_3$

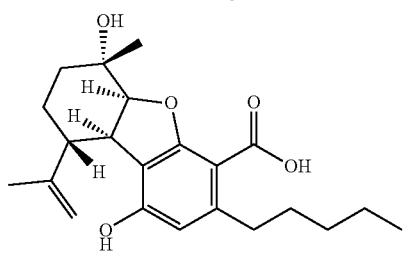

(5aS,6S,9R,9aR)-
Cannabielsoic acid A
CBEA-C$_5$ A

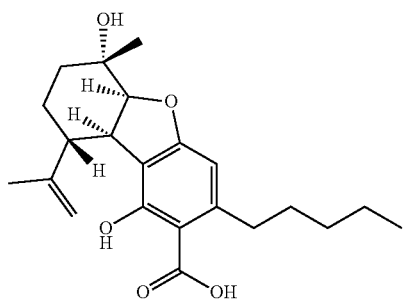

(5aS,6S,9R,9aR)-
Cannabielsoic acid B
CBEA-C$_5$ B

-continued

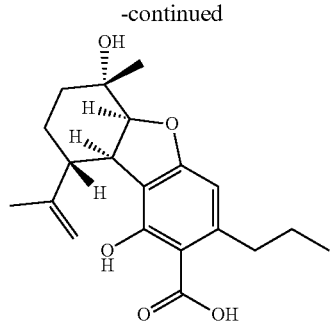

(5aS,6S,9R,9aR)-
C$_3$-Cannabielsoic acid B
CBEA-C$_5$ B

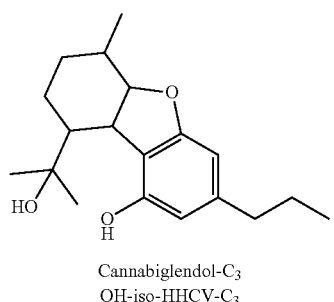

Cannabiglendol-C$_3$
OH-iso-HHCV-C$_3$

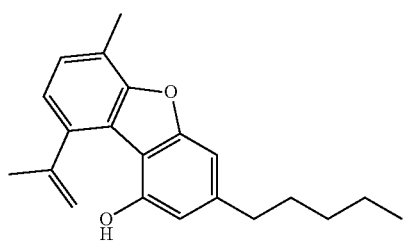

Dehydrocannabifuran
DCBF-C$_5$

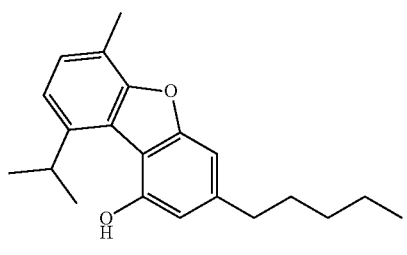

Cannabifuran
CBF-C$_5$

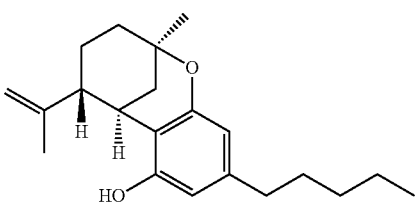

(-)-Δ$^7$-trans-(1R,3R,6R)-
Isotetrahydrocannabinol

-continued

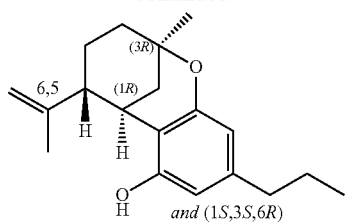

(±)-Δ⁷-1,2-cis-
(1R,3R,6S/1S,3S,6R)-
Isotetrahydro-
Cannabivarin

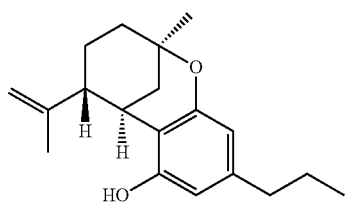

(−)-Δ⁷-trans-
(1R,3R,6R)-
Isotetrahydrocannabivarin

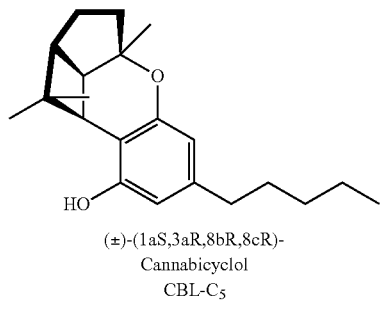

(±)-(1aS,3aR,8bR,8cR)-
Cannabicyclol
CBL-C₅

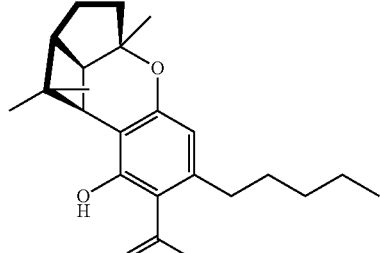

(±)-(1aS,3aR,8bR,8cR)-
Cannabicyclolic acid A
CBLA-C₅ A

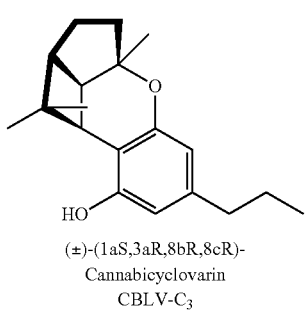

(±)-(1aS,3aR,8bR,8cR)-
Cannabicyclovarin
CBLV-C₃

-continued

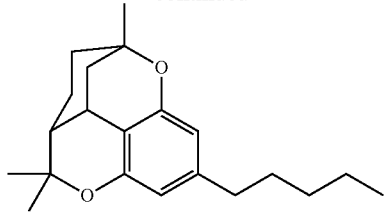

Cannabicitran
CBT-C₅

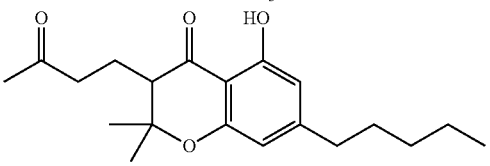

Cannabichromanone
CBCN-C₅

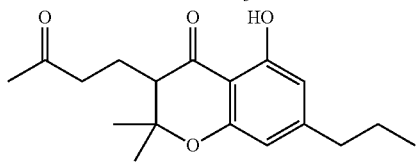

Cannabichromanone-C3
CBCN-C₃

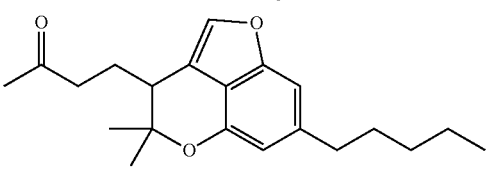

Cannabicoumaronone
CBCON-C₅

As used herein, the term "terpene" refers to hydrocarbons of biological origin having carbon skeletons formally derived from isoprene [CH2=C(CH3)CH=CH2]. This class is subdivided into the C5 hemiterpenes, C10 monoterpenes, C15 sesquiterpenes, C20 diterpenes, C25 sesterterpenes, C30 triterpenes, C40 tetraterpenes (carotenoids), and C5n polyterpenes.

As used herein, the term "terpenoid" refers to hydrocarbons of biological origin having carbon skeletons formally derived from isoprene [CH2=C(CH3)CH=CH2] and differing from terpenes in that one or more methyl groups have been moved or added, or an oxygen added compared to the terpene. Terpenoids are classified as follows: Hemiterpenoids, 1 isoprene unit (5 carbons); Monoterpenoids, 2 isoprene units (10 C); Sesquiterpenoids, 3 isoprene units (15 C); Diterpenoids, 4 isoprene units (20 C) (e.g. ginkgolides); Sesterterpenoids, 5 isoprene units (25 C); Triterpenoids, 6 isoprene units (30 C) (e.g. sterols); Tetraterpenoids, 8 isoprene units (40 C) (e.g. carotenoids); and Polyterpenoids (larger number of isoprene units). Examples of terpenoids found in *Cannabis* include, but are not limited to, Limonene, α-Pinene, β-Myrcene, Linolool, β-Caryophyllene, Carophyllene oxide, Nerolidol, and Phytol.

As used herein, the term "solvent extract" refers to a composition provided by solvent extraction of a starting material such as *Cannabis* plant material or trichomes. The solvent extract may preferably have the solvent substantially removed from the extract, for example by evaporation.

As used herein, the term "enriched for" when used in reference to a composition means that one or more specified compounds are present in a higher concentration, commonly expressed as a weight/weight percentage, as compared to a starting material, such as *Cannabis* plant material or trichomes.

As used herein the term "concentrate" when used in reference to a composition containing one or more compounds means that the one or more compounds are concentrated in the composition on a weight/weight basis as compared to a starting material, such as *Cannabis* plant material or trichomes.

As used herein, the term "substantially free of THC-type compounds" refers to extracts, fractions or other preparations from a *Cannabis* plant that contain less than 2%, preferably less than 1%, more preferably less than 0.5%, and most preferably less than 0.1% Tetrahydrocannabinol-type (THC) compounds (e.g., $\Delta^9$-Tetrahydrocannabinol $\Delta^9$-THC-C5, $\Delta^9$-Tetrahydrocannabinol-$C_4$ $\Delta^9$-THC-$C_4$, $\Delta^9$-Tetrahydrocannabivarin $\Delta^9$-THCV-$C_3$, $\Delta^9$-Tetrahydrocannabiorcol $\Delta^9$-THCO-$C_1$, $\Delta^9$-Tetrahydrocannabinolic acid A $\Delta^9$-THCA-$C_5$ A, $\Delta^9$-Tetrahydrocannabinolic acid B, $\Delta^9$-THCA-$C_5$ B, $\Delta^9$-Tetrahydrocannabinolic acid-$C_4$ A and/or B $\Delta^9$-THCA-$C_4$ A and/or B, $\Delta^9$-Tetrahydro-cannabivarinic acid A $\Delta^9$-THCVA-$C_3$ A, $\Delta^9$-Tetrahydrocannabiorcolic acid A and/or B $\Delta^9$-THCOA-$C_1$ A and/or B), (-)-$\Delta^8$-trans-(6aR,10aR)-$\Delta^8$-Tetrahydrocannabinol $\Delta^8$-THC-$C_5$, (-)-$\Delta^8$-trans-(6aR, 10aR)-Tetrahydrocannabinolic acid A $\Delta^8$-THCA-$C_5$ A, (-)-(6aS,10aR)-$\Delta^9$-Tetrahydrocannabinol (-)-cis-$\Delta^9$-THC-$C_5$).

As used herein, the term "phytonutrient" refers to organic compounds isolated from plants that have a biological effect, and includes, but is not limited to, compounds of the following classes: cannabinoids. isoflavonoids, oligomeric proanthcyanidins, indol-3-carbinol, sulforaphone, fibrous ligands, plant phytosterols, ferulic acid, anthocyanocides, triterpenes, omega 3/6 fatty acids, polyacetylene, quinones, terpenes, cathechins, gallates, and quercitin.

As used herein, the term "functional foods" refers to food products that include biologically active nutraceutical agents.

As used herein, the terms "nutraceutical agent," and related terms, refer to natural, bioactive chemical compounds that have health promoting, disease preventing or medicinal properties. Examples of nutraceutical agents include, but are not limited to, extracts from *Allium Cepa, Allium Sativum, Aloe Vera, Angelica* Species, Naturally Occurring Antioxidants, *Aspergillus Oryzae* Enzyme Therapy, barley grass, Bromelain, Carnitine, Carotenoids and Flavonoids, Catechin, *Centella Asiatica* (Gotu *kola*), Coenzyme Q10, Chinese Prepared Medicines, *Coleus Forskohlii, Commiphora Mukul, Crataegus Oxyacantha* (Hawthorne), *Curcuma Longa* (Turmeric), *Echinacea* Species (Purple Coneflower), *Eleutherococcus Senticosus* (Siberian Ginseng), *Ephedra* Species, Dietary Fish Oil Consumption and Fish Oil Supplementation, Genistein, *Ginkgo Biloba, Glycyrrhiza* (Licorice), *Hypericum* Perforatum (St. John's Wort), *Hydrastis* (Goldenseal) and Other Berberine-Containing Plants, *Lactobacillus, Lobelia* (Indian Tobacco), *Melaleuca Alternifolia, Mentha Piperita*, NGNA, *Panax Ginseng*, Pancreatic Enzymes, *Piper* Mythisticum, Procyanidolic Oligomers, *Pygeum Africanum*, Quercetin, *Sarsaparilla* Species, *Serenoa Repens* (Saw *palmetto, Sabal serrulata*), *Silybum Marianum* (Milk Thistle), Rosemary/Lemon balm, Selenite, *Tabebuia Avellanedae* (*LaPacho*), *Taraxacum Officinale, Tanacetum Parthenium* (Feverfew), *Taxol, Uva Ursi* (Bearberry), *Vaccinium Myrtillus* (Blueberry), *Valerian Officinalis, Viscum Album* (Mistletoe), Vitamin A, Beta-Carotene and Other Carotenoids, and *Zingiber Officinale*(Ginger).

As used herein, the terms "subject" and "patient" refer to any animal, such as a mammal like a dog, cat, bird, livestock, and preferably a human. Specific examples of "subjects" and "patients" include, but are not limited to, individuals suffering from viral obesity.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

As used herein, the term "foodstuff" refers to any substance fit for human or animal consumption.

As used herein, the term "dietary supplement" refers to a small amount of a compound for supplementation of a human or animal diet packaged in single or multiple dose units. Dietary supplements do not generally provide significant amounts of calories but may contain other micronutrients (e.g., vitamins or minerals).

As used herein, the term "nutritional supplement" refers to a composition comprising a "dietary supplement" in combination with a source of calories. In some embodiments, nutritional supplements are meal replacements or supplements (e.g., nutrient or energy bars or nutrient beverages or concentrates).

DETAILED DESCRIPTION OF THE INVENTION

The present invention relates to extracts and concentrates obtained from extraction from *Cannabis*, preferably cannabinoid and/or terpene concentrates, and formulation of the concentrates, particularly for use for direct vaporization, infusion into edible matrices, in electronic inhalation devices, and as nutraceuticals. The concentrates described herein may preferably be produced from either drug or industrial *Cannabis* species. The concentrates are preferably enriched for one or more cannabinoids and and/or terpenes as described in more detail below. The concentrates may be formulated in a variety of ways, with or without other phytonutrients or nutraceutical agents as also described in more detail below.

Disclosed herein are efficient methods to produce *cannabis* extracts with unique chemical properties using mechanical extraction followed by a solvent extraction. The extracts are then optionally processed by a whipping procedure to produce a finished extract with unique chemical and physical properties. The two-step extraction has many advantages over other techniques. The process allows for a higher throughput with less solvent waste because of the ability to obtain a much larger amount of finished extract from each solvent extraction pass. The final extracts are of a higher quality containing less water, chlorophyll, and other unwanted contaminants found in solvent extracts made directly from plant materials. The final extracts are also more visually appealing because of their lighter color. Another advantage is to allow for the first extraction to take place on fresh or freshly dried *Cannabis* after which the crude extract can be stored for great lengths of time before a solvent extraction takes place. Other methods produce a lower quality extract when significant time passes between the harvesting of the plant material and when it is processed.

The present invention further relates to extracts concentrates obtained from extraction from *cannabis*, preferably cannabinoid and/or terpene concentrates, wherein THC is converted to one or more natural CBN-type cannabinoids by an oxidizing treatment. The extracts and concentrates find use for direct vaporization, infusion into edible matrices, in electronic inhalation devices, and as nutraceuticals. The present invention relates to extracts concentrates obtained from extraction from *cannabis*, preferably cannabinoid and/or terpene concentrates, wherein THC is converted to one or more natural CBN-type cannabinoids by an oxidizing treatment. The extracts and concentrates find use for direct vaporization, infusion into edible matrices, in electronic inhalation devices, and as nutraceuticals. The concentrates described herein may preferably be produced from either drug or industrial *cannabis* species. The concentrates are preferably enriched for one or more cannabinoids, preferably CBN-type cannabinoids, and and/or terpenes as described in more detail below. The concentrates may be formulated in a variety of ways, with or without other phytonutrients or nutraceutical agents as also described in more detail below.

Disclosed herein are efficient methods to produce *cannabis* extracts with unique chemical properties using mechanical extraction followed by a solvent extraction and oxidation process. The extracts are then optionally processed by a whipping procedure to produce a finished extract with unique chemical and physical properties. The two-step extraction has many advantages over other techniques. The process allows for a higher throughput with less solvent waste because of the ability to obtain a much larger amount of finished extract from each solvent extraction pass. The final extracts are of a higher quality containing less water, chlorophyll, and other unwanted contaminants found in solvent extracts made directly from plant materials. The final extracts are also more visually appealing because of their lighter color. Another advantage is to allow for the first extraction to take place on fresh or freshly dried *cannabis* after which the crude extract can be stored for great lengths of time before a solvent extraction takes place. Other methods produce a lower quality extract when significant time passes between the harvesting of the plant material and when it is processed.

*Cannabis* produces the majority of its active ingredients (cannabinoids and terpenoids) in glandular trichomes found on the flowers, buds, leaves, and stalks of the plants. In preferred embodiments of the present invention, *Cannabis* plant material (e.g., flowers and leaves, either fresh or dried) containing glandular trichomes are processed mechanically to remove and concentrate the majority of these trichomes. Preferred processes separate the trichomes from the plant material by passing the trichomes through a mesh of appropriate size to allow the trichomes to pass through and exclude as much unwanted plant material as possible. The mesh may be made of any suitable material, e.g., stainless steel, aluminum, nylon, etc. Different varieties of *Cannabis* produce trichome heads of varying size, thus the optimal mesh size depends on the average size of the trichome heads being collected. In preferred embodiments, the processes of the present invention utilize mesh sizes ranging from 1 to 1000 microns in diameter, most preferably from 1 to 350 microns in diameter. One or multiple layers of mesh may be utilized. The use of multiple layers of mesh can help to further separate the desired trichomes from unwanted particles of plant material that are either slightly smaller or slightly larger.

In some embodiments, the mechanical trichome concentration processes utilize a cylindrical mesh drum driven by a belt and motor. The plant material is placed in the drum, the drum is rotated, and the trichomes are expelled from the drum through the mesh pores. In some embodiments, the plant material is frozen (i.e., at $-20$ C to $-70$ C) prior to tumbling. In some embodiments, the plant material is tumbled in the presence of ice, preferably dry ice. In some embodiments, the mesh drum is rotated in an ice water bath. Both the dry and wet method yield trichome concentrates with high levels of bioactive compounds. When a wet process is used, excess liquid is preferably pressed from the trichome concentrate followed by drying.

The second step in the extraction process comprises solvent extraction of the trichome concentrate. Extracts are preferably produced using a solvent recovery apparatus. For gaseous organic solvent mixtures, a pressurized closed botanical extraction system is preferred. For carbon dioxide extraction, a supercritical or subcritical botanical extraction apparatus is preferred. For liquid organic solvent extraction, spray dryers and/or common vacuum distillation apparatuses are preferred. In preferred embodiments, the apparatus allows for as low temperature removal of solvents as possible to avoid unwanted decarboxylation and/or removal of terpene compounds from the extract.

In all methods, the solvent passes through the trichome concentrate either in a column packed with the trichome concentrate (as part of the solvent recovery apparatus or with a discrete step) or the trichome concentrate can be saturated with solvent for a defined amount of time followed by filtration. Optionally, the extraction can be assisted through the use of sonication, microwave assistance, mechanical mixing, or other similar processes.

Examples of useful extraction solvents include gaseous solvents, in a liquid state, either neat or as a mixture, such as propane, n butane, isobutylene and/or isobutane. Examples of preferred solvent mixtures include 40-80% isobutane, 60-10% propane, and 20-5% n butane. Other mixtures can reverse these ratios. Examples of preferred liquid (normal T and P) extraction solvents include pentane, isopentane, hexanes (all structural isomers), ethyl acetate, ethanol, isopropanol, and heptanes (all structural isomers). Carbon dioxide in a supercritical or subcritical state is also a preferred solvent for the processes of the present invention. Other preferred solvent extraction mixtures include mixtures of isobutane and/or pentane with liquid nitrogen passed through the plant material followed by an optional sieve with pore diameters from 50 to 1000 microns.

After the solvent has been passed through the plant material, a filter or several filter steps can optionally be performed to avoid passing plant material from the crude extract into the final elute. The filter(s) can take many forms and have a wide range of pore sizes. Preferred filters include, but are not limited to, Teflon filters, sintered glass, paper, metal mesh, and the like.

Additional bioactive compounds, phytonutrients, nutraceutical agents, flavoring agents and the like may be added to the *Cannabis* solvent extract either before or after solvent removal and concentration. Examples of additives include, but are not limited to, terpene/terpenoid compounds, other essential oils, natural or artificial flavorings, edible or food grade carrier solvents such as propylene glycol, glycerin, triacetin, food oils, topical oils and butters, etc. Additives are described in more detail below. Solubilizers, suspension agents, and uptake promoters such as beta-cyclodextrins may also be added before or after solvent removal.

In preferred embodiments, solvent is removed from the solvent extract to provide a concentrate. Suitable processes for solvent removal include, but are not limited to, solvent exchange, vacuum distillation, vacuum desiccation, TFE, or crystallization of active ingredients. Solvent removal may take place at a wide range of temperatures consistent with the process used.

The extracts can optionally be further processed to concentrate desired bioactive agents or remove undesired compounds (e.g., contaminants). In some embodiments, the extract or eluate is passed through a preparatory or industrial scale column with stationary phases, for example, silica, alumina, C8, or C18 stationary phases. A number of solvent matrices may be utilized. Gradients may optionally be used to alter the polarity of mobile phases to facilitate this step. Examples of preferred systems include mixtures of hexane (s), heptane(s), pentane(s), ethyl acetate, and/or ethanol. Fractions can be collected containing desired compounds, and combined if desired. The solvent is then removed as described above.

In some embodiments, target compounds (either desired or undesired) are removed from solution by crystallization. Crystallization comprises concentrating the eluate (with an additional optional solvent exchange) to a preferably non polar solvent (e.g., heptane(s), hexane(s), pentane(s)). The concentrated solvent/extract mixture can be cooled to −20 to −200 C to facilitate crystallization. Optional crystallization initiators may be incorporated into the process. Once crystallization has occurred, the crystals are filtered and depending on whether the eluate or crystal products are desired, one or the other can be discarded and desired product can be passed through to additional steps for further processing or used as a final product.

In some embodiments, the extract or extract is further refined prior to final processing. In some embodiments, the extract is vacuum distilled to near dryness then taken up in ethanol or another alcohol or polar solvent (the solvent solution may be optionally heated). The ethanol solution is cooled overnight to −20 C+/−20 degrees after which undesirable fats, lipids and waxes will precipitate out of the solution and can be filtered using common methods. In some embodiments, chlorophyll which provides a slight greenish to black hue, is removed from the extract. In these embodiments, the extract is taken up in a solvent then exposed to UV light for 30 minutes to 24 hours to break down remaining chlorophyll, which will turn from green to amber colors. If the color is still not desirable, activated carbon may be added to the ethanol solution. Additional solvents may also be utilized. In these embodiments, the extract and activated carbon are agitated together for several hours or days then the extract is filtered out of the activated carbon. The solvent may then be removed. In some embodiments, a final washing step is beneficial to remove any remaining impurities. In some embodiments, a highly concentrated extract (regardless of the solvent it is dissolved in) is mixed with a non-polar solvent such as pentane, hexane, or heptane. Equal amounts of a concentrated brine solution are then added. The solution is agitated vigorously then the brine solution is decanted. This process may preferably be repeated several times. This step may be followed with an optional water wash. The extract may then be treated with sodium sulfate or another suitable desiccant to remove water.

In some embodiments, the extract or concentrate obtained as described above may be further processed, for example by adding one or more bioactive compounds or nutraceutical agents or by further concentrating a target compound in the Cannabis extract. Further concentration may be preferably accomplished by column chromatography or crystallization as described above. In some preferred embodiments, the extracts are mechanically processed to provide a composition with desired physiochemical properties. In some embodiments, extracts are homogenized by shear force mixing. Suitable mixing devices include, but are not limited to, magnetic stir bar apparatuses, wire whisk devices, augers, and the like. Preferably, the extract is mixed (e.g., whisked or whipped) until dry. The final product preferably has a wax or clay-like consistency, is white to slightly yellow in color, and is opaque.

In other embodiments, spray drying is used to provide a fluffy crystalline extract of white to yellow or amber color. In this process, the Cannabis extract is sprayed into a fine mist inside of a vacuum chamber. The system is preferably configured to facilitate the evaporation of solvent from the fine mist leaving behind very fine crystalline cannabinoid extract that can be collected in final form containing from 30-99% cannabinoids, preferably from about 55% to 99% cannabinoids, and most preferably from about 65% to 99% cannabinoids. In other embodiments, thin film evaporation techniques are utilized. In some embodiments, these methods comprise spreading a thin layer of concentrated extract on a surface and placing the surface inside of a vacuum oven and/or desiccator. Once the solvent has been removed, a white to yellow or amber or dark colored extract remains. This extract preferably has a semicrystalline consistency. This product can be milled (preferably cryogenically milled) to produce a powder or divided into portions for easy handling.

The extracts described above can preferably be pressed into standardized pellets through compaction, with or without heat. These pellets preferably provide a standardized size, weight of cannabinoid extract. The pellets can be packaged in blister pack, plastic jar, or a glass jar.

The concentrates of the present invention are preferably enriched for one or more bioactive compounds from Cannabis. In some embodiments, the concentrates of the present invention are preferably enriched for one or more cannabinoids. Preferred cannabinoid compounds include, but are not limited to: Cannabigerol-type (CBG) compounds (e.g., Cannabigerol (E)-CBG-$C_5$, Cannabigerol monomethyl ether (E)-CBGM-$C_5$ A, Cannabigerolic acid A (Z)-CBGA-$C_5$ A, Cannabigerovarin (E)-CBGV-$C_3$, Cannabigerolic acid A (E)-CBGA-$C_5$ A, Cannabigerolic acid A monomethyl ether (E)-CBGAM-$C_5$ A and Cannabigerovarinic acid A (E)-CBGVA-$C_3$ A); Cannabichromene-type (CBC) type compounds (e.g., (±)-Cannabichromene CBC-$C_5$, (±)-Cannabichromenic acid A CBCA-$C_5$ A, (±)-Cannabivarichromene, (±)-Cannabichromevarin CBCV-$C_3$, (±)-Cannabichromevarinic acid A CBCVA-$C_3$ A); Cannabidiol-type (CBD) compounds (e.g., (−)-Cannabidiol CBD-$C_5$, Cannabidiol momomethyl ether CBDM-$C_5$, Cannabidiol-$C_4$ CBD-$C_4$, (−)-Cannabidivarin CBDV-$C_3$, Cannabidiorcol CBD-$C_1$, Cannabidiolic acid CBDA-$C_5$, Cannabidivarinic acid CBDVA-$C_3$); Cannabinodiol-type (CBND) compounds (e.g., Cannabinodiol CBND-$C_5$, Cannabinodivarin CBND-$C_3$); Tetrahydrocannabinol-type (THC) compounds (e.g., $\Delta^9$-Tetrahydrocannabinol $\Delta^9$-THC-$C_5$, $\Delta^9$-Tetrahydrocannabinol-$C_4$ $\Delta^9$-THC-$C_4$, $\Delta^9$-Tetrahydrocannabivarin $\Delta^9$-THCV-$C_3$, $\Delta^9$-Tetrahydrocannabiorcol, $\Delta^9$-THCO-$C_1$, $\Delta^9$-Tetrahydrocannabinolic acid A $\Delta^9$-THCA-$C_5$ A, $\Delta^9$-Tetrahydrocannabinolic acid B, $\Delta^9$-THCA-$C_5$ B, $\Delta^9$-Tetrahydrocannabinolic acid-$C_4$ A and/or B $\Delta^9$-THCA-$C_4$ A and/or B, $\Delta^9$-Tetrahydro-cannabivarinic acid A $\Delta^9$-THCVA-$C_3$ A, $\Delta^9$-Tetrahydrocannabiorcolic acid A and/or B $\Delta^9$-THCOA-$C_1$ A and/or B), (−)-$\Delta^8$-trans-(6aR,10aR)-$\Delta^8$-Tetrahydrocannabinol $\Delta^8$ THC-$C_5$, (−)-$\Delta^8$-trans-(6aR,10aR)-Tetrahydrocannabinolic acid A $\Delta^8$-THCA-$C_5$ A, (−)-(6aS,10aR)-$\Delta^9$-Tetrahydrocannabinol (−)-cis-$\Delta^9$-THC-$C_5$); Cannabinol-type (CBN) type compounds (e.g., Cannabinol CBN-$C_5$, Cannabinol-$C_4$ CBN-$C_4$, Cannabivarin CBN-$C_3$, Cannabinol-$C_2$ CBN-$C_2$, Cannabiorcol CBN-$C_1$, Cannabinolic acid A CBNA-$C_5$ A, Cannabinol methyl ether CBNM-$C_5$, (−)-(9R,10R)-trans-Cannabitriol (−)-trans-CBT-$C_5$, (+)-(9S,10S)-Cannabitriol (+)-trans-CBT-$C_5$, (±)-(9R,10S/9S,10R)-); Cannabitriol-type (CBT) compounds (e.g., Cannabitriol (±)-cis-CBT-C5, (−)-(9R,10R)-trans-10-O-Ethyl-cannabitriol (−)-trans-CBT-OEt-C5, (±)-(9R,10R/9S,10S)-Cannabitriol-C3(±)-trans-CBT-C3, 8,9-Dihydroxy-$\Delta^{6a(10a)}$-tetrahydrocannabinol 8,9-Di-OH-CBT-C5, Cannabidiolic acid A cannabitriol ester CBDA-$C_5$ 9-OH-CBT-$C_5$ ester, (−)-(6aR,9S,10S,10aR)-9,10-Dihydroxy-hexahydrocannabinol, Cannabiripsol, Cannabiripsol-$C_5$, (−)-6a,7,10a-Trihydroxy-$\Delta^9$-tetrahydrocannabinol (−)-Cannabitetrol, 10-Oxo-$\Delta^{6a(10a)}$tetrahydrocannabinol OTHC); Cannabielsoin-type (CBE) compounds (e.g., (5aS,6S,9R,9aR)-Cannabielsoin CBE-$C_5$, (5aS,6S,9R,9aR)-$C_3$-Cannabielsoin CBE-$C_3$, (5aS,6S,9R,9aR)-Cannabielsoic acid A CBEA-$C_5$ A, (5aS,6S,9R,9aR)-Cannabielsoic acid B CBEA-$C_5$ B; (5aS,6S,9R,9aR)-$C_3$-Cannabielsoic acid B CBEA-$C_3$ B, Cannabiglendol-$C_3$ OH-iso-HHCV-$C_3$, Dehydrocannabifuran DCBF-$C_5$, Cannabifuran CBF-$C_5$) Isocannabinoids compounds (e.g., (−)-$\Delta^7$-trans-(1R,3R,6R)-Isotetrahydrocannabinol, (±)-$\Delta^7$-1,2-cis-(1R,3R,6S/1S,3S,6R)-Isotetrahydrocannabivarin, (−)-$\Delta^7$-trans-(1R,3R,6R)-Isotetrahydrocannabivarin); Cannabicyclol-type (CBL) compounds (e.g., (±)-(1aS,3aR,8bR,8cR)-Cannabiaycyclol CBL-C5, (±)-(1aS,3aR,8bR,8cR)-Cannabicyclolic acid A CBLA-$C_5$ A, (±)-(1aS,3aR,8bR,8cR)-Cannabicyclovarin CBLV-C3; Cannabicitran-type (CBT) compounds (e.g., Cannabicitran CBT-$C_5$); or Cannabichromanone-type (CBCN) compounds (e.g., Cannabichromanone CBCN-$C_5$, Cannabichromanone-C3 CBCN-$C_3$, Cannabicoumaronone CBCON-$C_5$). In some embodiments, the composition comprise greater than about 0.5%, 1%, 2%, 5%, 10%, 20%, 30%, 40%, 50%, 60%, 70%, 80%, 90%, 95% or 99% w/w of one of the foregoing compounds. In some embodiments, the compositions comprise from 0.5%, 1%, 2%, 5%, 10% or 20% w/w to about 25%, 30%, 40% or 50% w/w of one of the foregoing compounds. In some embodiments, the concentrates of the present invention are co-enriched for one or more of the foregoing compounds, for example, 2, 3, 4, 5, 6, 7, 8, 9 or 10 of the compounds. For example, in some embodiments, the concentrates comprise from about 0.5%, 1%, 2%, or 5% w/w to about 10% or 20% w/w of a combination of the foregoing compounds. In some embodiments, the compositions are essentially free of THC-type cannabinoid compounds. In some embodiments, the compositions are essentially free of CBN-type compounds. Thus, in some embodiments, the concentrates of the present invention are enriched (as specified by the percentages above) for one or more cannabinoids as described, with the proviso that the cannabinoids are not THC-type cannabinoid or CBN-type cannabinoid. In some embodiments, the concentrates are enriched for one or more Cannabigerol-type (CBG) compounds; Cannabichromene-type (CBC) type compounds; Cannabidiol-type (CBD) compounds; Cannabinodiol-type (CBND) compounds; Cannabielsoin-type (CBE) compounds; Isocannabinoids compounds; Cannabicyclol-type (CBL) compounds; Cannabicitran-type (CBT) compounds; or Cannabichromanone-type (CBCN) compounds.

In some embodiments, the concentrates of the present invention are co-enriched for one or more cannabinoid compounds (in the combinations and w/w percentages described above) and one or more terpenoids. The terpenoids are preferably elected from one or more of alloaromadendrene, allyl hexanoate, benzaldehyde, (Z)-α-cis-bergamotene, (Z)-α-trans-bergamotene, β-bisabolol, epi-α-bisabolol, β-bisabolene, borneol (camphol), cis-γ-bisabolene, borneol acetate (bornyl acetate), α-cadinene, camphene, camphor, cis-carveol, caryophyllene (β-caryophyllene), α-humulene (α-caryophyllene), γ-cadinene, Δ-3-carene, caryophyllene oxide, 1,8-cineole, citral A, citral B, cinnameldehyde, α-copaene (aglaiene), γ-curcumene, cymene, β-elemene, γ-elemene, ethyl decdienoate, ethyl maltol, ethyl propionate, ethylvanillin, eucalyptol, α-eudesmol, β-eudesmol, γ-eudesmol, eugenol, cis-β-farnesene ((Z)-β-farnesene), trans-α-farnesene, trans-β-farnesene, trans-γ bisabolene, fenchone, fenchol (norbornanol, β-fenchol), geraniol, α-guaiene, guaiol, methyl anthranilate, methyl salicylate, 2-methyl-4-heptanone, 3-methyl-4-heptanone, hexyl acetate, ipsdienol, isoamyl acetate, lemenol, limonene, d-limonene (limonene), linolool (linalyl alcohol, β-linolool), α-longipinene, menthol, γ-muurolene, myrcene (β-myrcene), nerolidol, trans-nerolidol, nerol, β-ocimene (cis-ocimene), octyl acetate, α-phellandrene, phytol, α-pinene (2-pinene), β-pinene, pulegone, sabinene, cis-sabinene hydrate (cis-thujanol), β-selinene, α-selinene, γ-terpinene, terpinolene (isoterpine), terpineol (α terpineol), terpineol-4-ol, α-terpinene (terpilene), α-thujene (origanene), vanillin, viridiflorene (ledene), and α-ylange. In some embodiments, the concentrates one or more cannabinoid compounds (in the combinations and w/w percentages described above) in combination with from 0.1%, 0.5%, 1%, 2%, 3% to about 5% or 10% of one or more of Alloaromadendrene, allyl hexanoate, benzaldehyde, (Z)-α-cis-bergamotene, (Z)-α-trans-bergamotene, β-bisabolol, epi-α-bisabolol, β-bisabolene, borneol (camphol), cis-γ-bisabolene, borneol acetate (bornyl acetate), α-cadinene, camphene, camphor, cis-carveol, caryophyllene (β-caryophyllene), α-humulene (α-caryophyllene), γ-cadinene, Δ-β-carene, caryophyllene oxide, 1,8-cineole, citral A, citral B, cinnameldehyde, α-copaene (aglaiene), γ-curcumene, β-cymene, β-elemene, γ-elemene, ethyl decdienoate, ethyl maltol, ethyl propionate, ethylvanillin, eucalyptol, α-eudesmol, β-eudesmol, γ-eudesmol, eugenol, cis-β-farnesene ((Z)-β-farnesene), trans-α-farnesene, trans-β-farnesene, trans-γbisabolene, fenchone, fenchol (norbornanol, β-fenchol), geraniol, α-guaiene, guaiol, methyl anthranilate, methyl salicylate, 2-methyl-4-heptanone, 3-methyl-4-heptanone, hexyl acetate, ipsdienol, isoamyl acetate, lemenol, limonene, d-limonene (limonene), linolool (linalyl alcohol, β-linolool), α-longipinene, menthol, γ-muurolene, myrcene (β-myrcene), nerolidol, trans-nerolidol, nerol, β-ocimene (cis-ocimene), octyl acetate, α-phellandrene, phytol, α-pinene (2-pinene), β-pinene, pulegone, sabinene, cis-sabinene hydrate (cis-thujanol), β-selinene, α-selinene, γ-terpinene, terpinolene (isoterpine), terpineol (α terpineol), terpineol-4-ol, α-terpinene (terpilene), α-thujene (origanene), vanillin, viridiflorene (ledene), and α-ylange.

In some embodiments, the present invention provides concentrates and extracts that are treated to convert THC-type cannabinoids into CBN-type cannabinoids. The concentrates and extracts are preferably produced as described above. In preferred embodiments, the concentrates and extracts are substantially free of THC-type cannabinoids. In some embodiments, the extracts and concentrates comprise less than 5%, 4%, 3%, 2%, 1%, 0.5% or 0.1% w/w THC-type cannabinoids. In some embodiments, the extracts and concentrates are enriched for one or more CBN-type cannabinoids. In some embodiments, the CBN-type cannabinoids are selected from Cannabinol CBN-$C_5$, Cannabinol-$C_4$ CBN-$C_4$, Cannabivarin CBN-$C_3$, Cannabinol-$C_2$ CBN-$C_2$, Cannabiorcol CBN-$C_1$, Cannabinolic acid A CBNA-$C_5$ A, and Cannabinol methyl ether CBNM-$C_5$. In some embodiments, the concentrates comprise greater than 20%, 30%, 40%, 50%, 60%, 70%, 80%, 90% or 95% w/w of one or more (e.g., 2, 3, 4, or 5) CBN-type cannabinoids. In some embodiments, the concentrates are co-enriched for one or more terpenoids. The terpenoids are preferably selected from one or more of Alloaromadendrene, allyl hexanoate, benzaldehyde, (Z)-α-cis-bergamotene, (Z)-α-trans-bergamotene, β-bisabolol, epi-α-bisabolol, β-bisabolene, borneol (camphol), cis-γ-bisabolene, borneol acetate (bornyl acetate), α-cadinene, camphene, camphor, cis-carveol, caryophyllene (β-caryophyllene), α-humulene (α-caryophyllene), γ-cadinene, Δ-3-carene, caryophyllene oxide, 1,8-cineole, citral A, citral B, cinnameldehyde, α-copaene (aglaiene), γ-curcumene, β-cymene, β-elemene, γ-elemene, ethyl decdienoate, ethyl maltol, ethyl propionate, ethylvanillin, eucalyptol, α-eudesmol, β-eudesmol, γ-eudesmol, eugenol, cis-β-farnesene ((Z)-β-farnesene), trans-α-farnesene, trans-β-farnesene, trans-γ bisabolene, fenchone, fenchol (norbornanol, β-fenchol), geraniol, α-guaiene, guaiol, methyl anthranilate, methyl salicylate, 2-methyl-4-heptanone, 3-methyl-4-heptanone, hexyl acetate, ipsdienol, isoamyl acetate, lemenol, limonene, d-limonene (limonene), linolool (linalyl alcohol, β-linolool), α-longipinene, menthol, γ-muurolene, myrcene (β-myrcene), nerolidol, trans-nerolidol, nerol, β-ocimene (cis-ocimene), octyl acetate, α-phellandrene, phytol, α-pinene (2-pinene), β-pinene, pulegone, sabinene, cis-sabinene hydrate (cis-thujanol), β-selinene, α-selinene, γ-terpinene, terpinolene (isoterpine), terpineol (α terpineol), terpineol-4-ol, α-terpinene (terpilene), α-thujene (origanene), vanillin, viridiflorene (ledene), α-ylangene. In some embodiments, the concentrates one or more cannabinoid compounds (in the combinations and w/w percentages described above) in combination with from 0.1%, 0.5%, 1%, 2%, 3% to about 5% or 10% of one or more of the terpenoids.

In some embodiments, the concentrate comprise a total cannabinoid fraction of from about 45% to 98% w/w (calculated as a weight percentage of the total weight of the concentrate), most preferably about 65% to 95% w/w total cannabinoid compounds and a total terpenoid fraction of from about 0.1% to 5% w/w total terpenoids (calculated as a weight percentage of the total weight of the concentrate). In some embodiments, the total cannabinoid fraction contains from about 62% to about 92% w/w or from about 75% to 92% w/w TCHA and THC combined (calculated as a weight percentage of the total weight of the concentrate). In other embodiments, the total cannabinoid fraction comprises from about 40% to 95% w/w or from about 60% to 92% w/w of a combination of CBG, CBC and THCV (calculated as a weight percentage of the total weight of the concentrate). As described above, the total cannabinoid fraction may additionally comprise at least 1%, 2%, 5%, or 10% w/w of three of the cannabinoid compounds (calculated as a weight percentage of the total weight of the concentrate). In some embodiments, the concentrate comprises at least 1%, 2%, 5%, or 10% w/w of four of the cannabinoid compounds (calculated as a weight percentage of the total weight of the concentrate). In some embodiments, the concentrate comprises at least 1%, 2%, 5%, or 10% w/w of five of the cannabinoid compounds. Likewise, the total terpenoid fraction may additionally comprise at least 0.05%, 0.1%, 0.2%, or 0.5% w/w of two of the terpenoids (calculated as a weight percentage of the total weight of the concentrate). In some embodiments, the total terpenoid fraction may additionally comprise at least 0.05%, 0.1%, 0.2%, or 0.5% w/w of three of the terpenoids (calculated as a weight percentage of the total weight of the concentrate). In some embodiments, the total terpenoid fraction may additionally comprise at least 0.05%, 0.1%, 0.2%, or 0.5% w/w of four of the terpenoids (calculated as a weight percentage of the total weight of the concentrate). In some embodiments, the total terpenoid fraction may additionally comprise at least 0.05%, 0.1%, 0.2%, or 0.5% w/w of five of the terpenoids (calculated as a weight percentage of the total weight of the concentrate).

In some preferred embodiments, the processes of the present invention utilize natural or pharmaceutically acceptable oxidizing agents to quickly oxidize a high THC cannabinoid extract to contain high levels of cannabinol. The oxidation procedure may be conducted at any time during the extraction or concentration process steps described above. In some embodiments, a high THC(a) extract is utilized in the process with or without an optional decarboxylation step (heating or chemical) to convert the THC(a) to THC before the oxidation step. In some preferred embodiments, the extract or concentrate is dissolved in a solvent (e.g., ethanol). Next, an oxidizing agent is added. Preferred oxidizing agents include hydrogen peroxide and ozone, which can be preferably used without heating. Other suitable oxidizing agents include, but are not limited to halogens, sulfuric acid, peroxydisulfuric acid, permanganate compounds, nitrous oxide, and the like. In some embodiments, more than 10%, 20, 30%, 40%, 50%, 60%, 70%, 80%, 90% or 95% of the THC in the extract or concentrate is converted to a CBN-type cannabinoid.

In some embodiments, the converted concentrates comprise a total cannabinoid fraction of from about 45% to 98% w/w (calculated as a weight percentage of the total weight of the concentrate), most preferably about 65% to 95% w/w total CBN-type compounds (e.g., as listed above) and a total terpenoid fraction of from about 0.1% to 5% w/w total terpenoids (e.g., as listed above; calculated as a weight percentage of the total weight of the concentrate). In some embodiments, the total cannabinoid fraction contains from about 62% to about 92% w/w or from about 75% to 92% w/w CBN-type compounds (calculated as a weight percentage of the total weight of the concentrate). As described above, the total cannabinoid fraction may additionally comprise at least 1%, 2%, 5%, or 10% w/w of three or more of the cannabinoid compounds (calculated as a weight percentage of the total weight of the concentrate). In some embodiments, the concentrate comprises at least 1%, 2%, 5%, or 10% w/w of four or more of the cannabinoid compounds (calculated as a weight percentage of the total weight of the concentrate). In some embodiments, the concentrate comprises at least 1%, 2%, 5%, or 10% w/w of five or more of the cannabinoid compounds. Likewise, the total terpenoid fraction may additionally comprise at least 0.01%, 0.05%, 0.1%, 0.2%, or 0.5% w/w of two or more of the terpenoids (calculated as a weight percentage of the total weight of the concentrate). In some embodiments, the total terpenoid fraction may additionally comprise at least 0.01%, 0.05%, 0.1%, 0.2%, or 0.5% w/w of three or more of the terpenoids (calculated as a weight percentage of the total weight of the concentrate). In some embodiments, the total terpenoid fraction may additionally comprise at least 0.01%, 0.05%, 0.1%, 0.2%, or 0.5% w/w of four or more of the terpenoids (calculated as a weight percentage of the total weight of the concentrate). In some embodiments, the total terpenoid fraction may additionally comprise at least 0.01%, 0.05%, 0.1%, 0.2%, or 0.5% w/w of five or more of the terpenoids (calculated as a weight percentage of the total weight of the concentrate). In some embodiments, the total terpenoid fraction may additionally comprise at least 0.01%, 0.05%, 0.1%, 0.2%, or 0.5% w/w of ten or more of the terpenoids (calculated as a weight percentage of the total weight of the concentrate). It should be noted that in defining the concentrates in weight percentage terms, the weight percentage of the combined components will not exceed 100%. It should be noted that in defining the concentrates in weight percentage terms, the weight percentage of the combined components will not exceed 100%.

In some embodiments, dry *cannabis* extracts or concentrates may be treated with ozone to effect oxidation. Ozone is a beneficial agent for processes where water is undesirable in the final product. Extracts or concentrates can likewise be treated with UV or visible light in the presence of oxygen. This is a slower process, less predictable, with lower efficiency. However, the advantage of this process is that there are no added chemicals or reagents and it can also be performed on 'dry' *cannabis* extracts.

The concentrates, extracts and converted extracts of the present invention may be formulated in a variety of ways. In some embodiments, the concentrates may be used either for smoking or in a vaporization system. In some embodiments, the mechanically mixed (e.g., whipped) products are particularly suitable for these uses. There are numerous devices on the market designed to vaporize *Cannabis* extracts for inhalation. The composition of the mechanically mixed product is such that it is easy to handle, visually unique and appealing due to the clay or wax-like consistency and light color. The concentrates also preferably are enriched for terpenoids that add the characteristic aroma of *Cannabis* flowers that is favored by consumers of these types of extracts.

In some embodiments, the concentrates are utilized as an active ingredient in a thin film delivery device for use as a sublingual or buccal delivery system. In preferred embodiments, the thin films are designed to be quick dissolving to administer a dose of 2 to 200 mg of the concentrates per application directly to the blood stream via adsorption through the buccal or oral mucosa. The thin films are preferably formed using standard solvent casting or heat extrusion techniques. The thin films optionally include a solubilizer, including one or more of the cyclodextrin compounds (including, but not limited to, β-cyclodextrin, α-cyclodextrin, γ-cyclodextrin, hydroxypropyl β-cyclodextrin, and randomly methylated β-cyclodextrin), one or more types of cyclodextrin polymers, liposomes, micelles, dendrimers, etc. In preferred embodiments, the increased solubility provided by the compound increases the bio-availability of the active ingredients. In preferred embodiments, the excipients used for construction of the film include a base polymer consisting of at least 35% w/v of the final products. For the base polymer one or more of the following common quick dissolving edible polymers is preferably used: hydroxyl propyl methyl cellulose (hypromellose, HPMC, Methocel, Metolose, Benecel), hydroxy propyl cellulose (hyprolose, Klucel, Nisso HPC), starch and modified starch (Amido, amylum, PharmGel, Fluftex W, Instant pure-Cote, Melogel,), pullulan (Pullulane, 1,6 a linked maltotriose), pectin (Citrus pectin, Methopectin, pectin, pectinic acid), gelatin (Byco, cryogel, Instagel, Solugel), and carboxy methyl cellulose (Akulell, Blanose, Aquasorb, CMC sodium).

In some embodiments, additional polymers are used to improve the properties of the thin film. Polymers that alter the disintegration properties of the film are used to make the thin film dissolve faster or more slowly. In some embodiments, mucoadhesive/bioadhesive polymers are optionally used to promote adhesion of the strip. These include xanthan gum, guar gum, locust bean gum, polycarbophil, cellulose derivatives, polyacyrlic acid, polycarbophil, and thiolated polymers. In some embodiments, plasticizers are used to reduce cracking or brittleness of the thin film by improving flexibility. Suitable plasticizers include maltodextrin, sorbitol, mannitol, glycerol, glycerine, propylene glycol, polyethylene glycols, triethyl citrate, tributyl citrate, acetyl citrate, triacetin, dimethyl phthalate, diethyl phthalate, dibutyl phthalate, castor oil, etc. In preferred embodiments, plasticizers are included from 5% to 30% w/v of the total formulation.

The thin film can preferably be designed for quick dissolution, or can comprise a polymer backing to slow the rate of dissolution. This allows for a more slow release into the target mucosal surface and discourages oral ingestion of the active ingredients.

The thin film may optionally include additional additives and excipients, such as taste-masking agents, flavoring agents, sweeteners, saliva stimulators, and hardening and thickening agents. These additives and excipients will generally be included in an amount of about 1% to 15% w/v of the thin film.

In some preferred embodiments, the present invention provides a chewing gum comprising a concentrate as described in detail above. The chewing gum may preferably be used as a health aid, natural treatment for medical symptoms, or for an intended psychoactive effect on the user and would be beneficial as a slow release oral mucosal or buccal delivery vehicle. In preferred embodiments, the chewing gum comprises from about 0.01 to 35% of a concentrate as described above. The chewing gum may preferably contain a sweetener (artificial or natural) as well as artificial and/or natural flavors. Optionally, the chewing gum can be coated with a shell consisting of sweetener, flavors, wetting agents, and solubility/bioavailability enhancers. The shell optionally contains cannabinoids. In preferred embodiments, the gum contains greater than 40% gum base. In some embodiments, the gum includes an optional solubilizer, for example, one or more of the cyclodextrin compounds (including, but not limited to, β-cyclodextrin, α-cyclodextrin, γ-cyclodextrin, hydroxypropyl β-cyclodextrin, and randomly methylated β-cyclodextrin), one or more types of cyclodextrin polymers, liposomes, micelles, dendrimers, etc. In preferred embodiments, the increased solubility provided by the compound increases the bio-availability of the active ingredients.

The present invention also encompasses other formulations of the concentrates. The concentrates may further be formulated with acceptable excipients and/or carriers for oral consumption. The carrier may be a liquid, gel, gelcap, capsule, powder, solid tablet (coated or non-coated), tea, or the like. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers further include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, Pa.). Such formulations may preferably comprise from about 1 to 200 mg of the concentrate. Where the formulation is an oral delivery vehicle such as a capsule or tablet, the oral delivery vehicle may preferably comprise from about 1 to 200 mg of the concentrate, 10 to 200 mg of the concentrate to 10 to 100 mg of the concentrate. A daily dosage may comprise 1, 2, 3, 4 or 5 of the oral delivery vehicles.

In other embodiments, the concentrates are provided as a powder or liquid suitable for adding by the consumer to a food or beverage. For example, in some embodiments, the concentrate can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food.

The concentrates of the present invention may be combined with one or more additional bioactive agents, phytonutrients, or nutraceutical agents to provide a dietary supplement. In some embodiments, the one or more additional bioactive agents, phytonutrients, or nutraceutical agents is from a source other than *Cannabis*. The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: ascorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), *spirulina*, zinc, and the like. Such optional ingredients may be either naturally occurring or concentrated forms. Nutraceutical agents are natural, bioactive chemical compounds that have health promoting, disease preventing or medicinal properties. Examples of nutraceutical agents that may be combined with the concentrates of the present invention include, but are not limited to, resveratrol, fucoidan, *Allium cepa, Allium sativum, Aloe vera, Angelica* Species, Naturally Occurring Antioxidants, *Aspergillus oryzae*, barley grass, Bromelain, Carnitine, carotenoids and flavonoids, Catechin, *Centella asiatica* (Gotu kola), Coenzyme Q10, Chinese Prepared Medicines, *Coleus forskohlii, Commiphora mukul*, Conjugated Linoleic Acids (CLAs), *Crataegus oxyacantha* (Hawthorne), *Curcuma longa* (Turmeric), *Echinacea* Species (Purple Coneflower), *Eleutherococcus senticosus* (Siberian *Ginseng*), *Ephedra* Species, Dietary Fish Oil, Genistein, *Ginkgo biloba, Glycyrrhiza* (Licorice), *Hypericum* perforatum (St. John's Wort), *Hydrastis* (Goldenseal) and other Berberine-containing plants, *Lactobacillus, Lobelia* (Indian Tobacco), *Melaleuca* alternifolia, Menaquinone, *Mentha piperita*, n-glycolylneuraminic acid (NGNA), *Panax Ginseng*, Pancreatic Enzymes, *Piper* mythisticum, Procyanidolic Oligomers, *Pygeum africanum*, Quercetin, *Sarsaparilla* species, *Serenoa repens* (Saw *palmetto, Sabal serrulata*), *Silybum marianum* (Milk Thistle), Rosemary/Lemon balm, Selenite, *Tabebuia avellanedae* (*LaPacho*), *Taraxacum officinale, Tanacetum parthenium* (Feverfew), Taxol, *Uva ursi* (Bearberry), *Vaccinium myrtillus* (Blueberry), *Valerian officinalis, Viscum* album (Mistletoe), Vitamin A, Beta-Carotene and other carotenoids, and *Zingiber officinale*(Ginger).

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guideline In other embodiments, the present invention provides nutritional supplements (e.g., energy bars or meal replacement bars or beverages) comprising a concentrate as described above. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See Modern Nutrition in Health and Disease, eighth edition, Lea & Febiger, publishers, 1986, especially Volume 1, pages 30-32.

The nutritional supplement can also contain other ingredients, such as one or a combination of other vitamins, minerals, antioxidants, fiber and other dietary supplements (e.g., protein, amino acids, choline, lecithin, omega-3 fatty acids). Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; betacarotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide.

Flavors, coloring agents, spices, nuts and the like can be incorporated into the product. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

In still further embodiments, the present invention provides functional foods, including food products, prepared food products, or foodstuffs comprising a concentrate as described above. For example, in some embodiments, beverages and solid or semi-solid foods comprising sulfated polysaccharides (e.g., fucoidan) are provided. These forms can include, but are not limited to, beverages (e.g., soft drinks, milk and other dairy drinks, and diet drinks), baked goods, puddings, dairy products, confections, snack foods, or frozen confections or novelties (e.g., ice cream, milk shakes), prepared frozen meals, candy, snack products (e.g., chips), soups, spreads, sauces, salad dressings, prepared meat products, cheese, yogurt and any other fat or oil containing foods, and food ingredients (e.g., wheat flour).

In preferred embodiments, an effective amount of the concentrate to cause the desired physiological response is provided to a subject, preferably in a once a day or twice a day dosage. In preferred embodiments, an effective amount of the concentrate is from 1-5000 mg of the concentrate, and most preferably from 100-2000 mg of the concentrate or 200 to 1000 mg of the concentrate daily. In some embodiments, the effective amount is the amount necessary to reduce inflammation, reduce pain, reduce nausea, enhance mood, produce a calm feeling, induce drowsiness or sleep, reduce anxiety, support joint health, support mental health, support anti-inflammatory response by the body, support brain function, support feelings of wellbeing, support healthy skin and reduce blemishes.

EXAMPLES

Example 1

Preparation of Trichome Concentrate

Method 1A

Materials and Methods

Equipment: A mechanical tumbler with a cylindrical barrel made of a steel mesh containing 170 micron pores. The barrel lies horizontally and is belt driven by an electric motor. The barrel portion is placed inside of a box with a collection pan at the bottom.

Methods: 200 g of dried *Cannabis* plant material from clones of the same variety of a drug strain of *Cannabis sativa* consisting of small flowers and trichome laden leaves was placed inside the tumbler and the motor turned on for differing lengths of time. The duration of extraction included 5 minutes, 15 minutes, one hour, and 6 hours. After the extraction, the trichome heads were collected as a dry powder in the bottom pan of the collection box.

This method can be extended to any process which agitates the plant material over a mesh screen to allow the trichome heads to fall through while catching the majority of plant material. Also, an optional step to freeze the plant material at −20 C to −70 C to cause the trichomes to be brittle before being placed in the tumbler was found to increase yield and improve quality of the extract. Dry ice was found to be a very suitable method for freezing the plant material because it prevented moisture buildup on the plant material. Pieces of dry ice can also be placed inside of the extraction tumbler to keep the plant material cold throughout the process and assist in agitation of the plant material were also found to be useful.

Results: The longer the duration of the extraction, the greater the yield of trichome heads. Yields per 200 g were from 11 g (5.5%) for the 5 minute extraction, 18 g (9%) for the 15 minute extraction, 22 g (11%) for the 1 hour extraction, to 29 g (14.5%) for the 6 hour extraction.

The concentration of cannabinoids as measured using HPLC/DAD decreased with increasing extraction times and yields. Total cannabinoids (THC+THCA+CBD+CBDA+CBN) concentrations ranged from 49% for the 5 minute extraction, 40% for the 15 minute extraction, 34% for the 1 hour extraction, and 26% for the 6 hour extraction.

The color of the collected heads ranged from light tan for the 5 minute extract to a darker, slightly greenish, brown for the 6 hour extraction.

Method 2A:

Materials: A large nylon cylinder was constructed of nylon mesh with a 180 micron pore diameter. The cylinder was entirely enclosed and a zipper was sewn in to allow access to the inside. A nylon bag large enough to fit the mesh cylinder inside of it was also constructed with a zipper to allow for access to the inside. The nylon used to construct this bag allowed water to penetrate but was woven tight enough to not allow any plant material or trichome heads to pass through.

Equipment: A large drum driven by a belt was mounted inside of a watertight container. The drum had several paddles mounted to the inside of the cylinder to provide for agitation of the contents. The apparatus was constructed to allow for the drum to be rotated through the top of the container while it was filled with water.

Method: 400 g of plant material was placed inside the mesh cylinder and it was zipped shut. The cylinder was zipped inside the bag and the bag was placed in the drum. The drum apparatus was filled ¾ of the way with ice water. The drum was rotated for 15 minutes, 30 minutes, and 1 hour. The bag was removed from the drum and allowed to drain of water.

The inner mesh bag was removed from the outer nylon bag. Inside the nylon bag, a medium light brown to dark, greenish brown, sediment had collected. The sediment was collected on a glass plate and excess water was pressed out using a 5 micron mesh nylon screen. The pressed trichome heads were placed on a glass plate and vacuum desiccated for 24 hours.

Results: Trends for this process were similar to the dry method, longer extraction times correlated to higher yields of extract. The yield (after drying) for the 15 minute extraction was 52 g (12%), for the 30 minute extraction it was 72 g (18%), and for the 1 hour extraction it was 89 g (22.3%).

The concentration of cannabinoids as measured using HPLC/DAD decreased with increasing extraction times and yields. Total cannabinoids (THC+THCA+CBD+CBDA+CBN) concentrations ranged from 58% for the 15 minute extraction, 52% for the 30 minute extraction, and 47% for the 1 hour extraction.

Example 2

Extraction from Trichome Concentrate

Method 1B
Gas Extraction

Materials and Equipment: A pressurized system was constructed with a solvent reservoir mounted on top of the column and separated by a operator controlled valve. The column consisted of a stainless steel cylinder with a valve pre-column leading to the reservoir and filter followed by another operator controlled valve post-column leading to a recovery chamber. The recovery chamber was outfitted with a heating mantle and an outlet valve to allow the solvent to be released back into the reservoir. All fitting and valves were airtight and explosion-proof.

Additional materials included tanks of propane, isobutane, and n-butane. All solvents were ultra-high purity grade and purchased from a chemical supplier.

200 grams of each of the crude extracts produced according to the methods in the previous description were used as well as 50 grams of plant material (trichome laden flower leaves and small flowers). Material A was produced by tumbling freshly dried plant material in the cylinder from Method 1, for 30 minutes. It was a light brown color and tested 46% total active cannabinoids by HPLC/DAD. Material B was produced by extracting freshly dried plant material in the ice water extraction equipment from Method 2 for 30 minutes. It was a medium brown in color and tested 59% total active cannabinoids. The crude extracts were made from the same plant material that was used for the experiment. All of the plant material (Material C) consisted of trichome dense small leaves and small *Cannabis* flowers and it originated from the same strain of drug-type *Cannabis sativa*. The homogenized plant material tested 14% total active cannabinoids.

Methods: Each of the samples was placed in the column. For the fixed size of the column, 200 g of the crude extract occupied approximately the same volume as 50 g of the plant material. Each extraction was carried out by passing 400 g of a propane, iso-butane, and n-butane mixture through the column packed with plant material or crude extract. The system was pressurized to ensure the gases were in kept in a liquid state while passing through the samples. The eluate was mostly stripped of solvent using the mechanism designed into the equipment. The remaining eluate was collected on glass petri dishes and placed in a vacuum desiccator.

Data: The dried extracts were amorphous solids, slightly sticky to touch, ranging from a translucent light yellow orange color for the extract made from Material A, to a translucent light amber color for Material B, to a darker translucent amber color for material C. Material A yielded 98.2 g of final extract with 89.6% active cannabinoids. Material B yielded 122.4 g of final extract with 87.4% active cannabinoids. Material C yielded 5.1 g of final extract that tested 79.0% active cannabinoids.

Method 2B
Liquid Extraction

Materials and Equipment: A vacuum distiller, n-Pentane, medium porosity sintered glass Buchner funnel with filter flask equipment. Various laboratory glassware was used. Three samples were used for this extraction 100 grams of each of the crude extracts produced according to the methods in the previous description were used as well as 100 grams of plant material (trichome laden flower leaves and small flowers). Material A was produced by tumbling freshly dried plant material in the cylinder from Method 1, for 30 minutes. It was a light brown color and tested 46% total active cannabinoids by HPLC/DAD. Material B was produced by extracting freshly dried plant material in the ice water extraction equipment from Method 2 for 30 minutes. It was a medium brown in color and tested 59% total active cannabinoids. The crude extracts were made from the same plant material that was used for the experiment. All of the plant material (Material C) consisted of trichome dense small leaves and small *Cannabis* flowers and it originated from the same strain of drug-type *Cannabis sativa*. The homogenized plant material tested 14% total active cannabinoids.

Method: The samples were each placed in 2 L of n-Pentane and lightly stirred for 30 seconds. Much less solvent (~200 ml) would have been needed for the pre-extracted samples, but 2 L was used for each sample in the interest of uniformity. 2 L was the minimum solvent needed to ensure all of the plant material was submerged in solvent. This demonstrates the inherent advantages of a two-step extraction with regard to minimizing solvent use and volumes necessary to work with. The samples were stirred in the solvent for a short period of time to avoid dissolving unwanted plant materials like chlorophyll.

The plant material was filtered out by pouring the solution through the Buchner funnel. The eluate was then stripped of n-Pentane using a rotary evaporator.

Data: The dried extracts were amorphous solids at STP slightly sticky to touch. With a slight warming, they become much more pliable and slightly runny. The extract produced with material A was much more translucent and lighter amber in color, the extract produced with material B was slightly darker but still translucent, the extract produced with material C was opaque and almost black. When held to the light, it had a green hue to it due to the increased chlorophyll content of this extract.

Material A yielded 50.2 g of final extract with 88.9% active cannabinoids. Material B yielded 63.0 g of final extract with 84.9% active cannabinoids. Material C yielded 9.2 g of final extract that tested 76.3% active cannabinoids.

Example 3

Processing of Extracts to Form a Waxy Base

Materials: Concentrated *Cannabis* extract eluate created from both Method 1A and Method 1B were utilized. Several whisk attachments were constructed. Some acceptable designs included magnetic stir bars, horizontal wires radiating from a central point attached to the shaft, an aerated design, an auger type configuration, an auger with a flat blade at the bottom, etc. The most successful design consisted of 6 wire "fish hooks" radiating from the central hub attached to the shaft.

Methods: The concentrated eluate is continuously stirred by the whisk. This occurred in a fume hood with vacuum desiccation due to the volatile nature of the solvent system. The eluate was placed in a Pyrex tray and the tray was maintained at 35 C in a water batch. The eluate was continuously whipped or whisked until dry. The whipped final product was a waxy or clay like consistency and had a white to yellow color. The product is opaque. The final product is not tacky to the touch and is much easier to handle than the unwhipped extracts. This waxy product base can optionally have additives mixed mechanically into the waxy base at this point.

Example 4

Oxidation of THC to CBN

Experiments using ozone, hydrogen peroxide, and UV/visible light exposure in the presence of oxygen have been able to produce significant amounts of cannabinol from THC or THCa in plant material (H2O2, light) and extracts (O3, H2O2, and light).

Materials and Equipment: Absolute ethanol, 30% concentrated hydrogen peroxide, several different pieces of common laboratory glassware and tools, temperature probe controlled magnetically stirred hot plates, common laboratory grade UV light used for reading TLC stains, analytical instruments for analysis (including balances, HPLC-DAD, and assorted volumetric measuring instruments) and *cannabis* extract produced using the above methods. The *cannabis* extract was decarboxylated using heat and measured for cannabinoid content. The extract measured 70.1% THC, 0.2% THCA, 0.2% CBN, 0.7% CBD, and 0.4% CBDA w/w. Analysis were performed using HPLC with a DAD detector, with an isocratic gradient of acetonitrile and water with formic acid, on a reverse phase C18 hplc column. All standards were purchased from Restek corporation.

Procedures: 200 ml of an ~50 mg/ml THC in ethanol solution was prepared by dissolving 14.27 g of the extract in 200 ml of absolute ethanol. 50 ml of the solution was measured and poured into two large, petri dishes which were labeled A and B. 50 ml of solution was measured and poured into a beaker and labeled C. The final 50 ml of solution was placed in a fourth beaker and labeled D. A and B were placed in petri dishes to maximize exposure to a top light source. A, B, C, and D were equipped with magnetic stir bars and placed on a stirring hotplate with the solution temperatures set to 40 C. A was placed in direct full spectrum sunlight for 12 hours at 40 C with stirring. B was placed under UV light for 12 hours at 40 C with stirring. To C was added 5 ml of the 30% hydrogen peroxide and stirred for 12 hours at 40 C in a low light environment. D was placed on a hot plate at 40 C with stirring and placed in a low light environment.

Results: Each sample other than D showed a marked increase in CBN levels. Baseline CBN levels for the stock solution were 0.1 mg/ml. Sample A measured 4.6 mg/ml of CBN, Sample B measured 3.5 mg/ml of CBN, Sample C measured 18.3 mg/ml of CBN, and Sample D measured 0.2 mg/ml of CBN.

The invention claimed is:

1. A chewing gum consisting essentially of at least 1% w/w each of an isolated cannabigerolic acid, isolated cannabichromenic acid and isolated cannabinol in a gum base.

2. The chewing gum of claim 1, further consisting essentially of at least 0.1% w/w each in the chewing gum of at least one terpenoid selected from the group consisting of Alloaromadendrene, allyl hexanoate, benzaldehyde, (Z)-a-cis-bergamotene, (Z)-a-trans-bergamotene, beta-bisabolol, epi-alpha-bisabolol, beta-bisabolene, borneol, c-gamma-bisabolene, borneol acetate, alpha-cadinene, camphene, camphor, cis-carveol, caryophyllene, alpha-humulene, gamma-cadinene, delta-3-carene, caryophyllene oxide, 1,8-cineole, citral A, citral B, cinnameldehyde, alpha-copaene, gamma-curcumene, beta-cymene, beta-elemene, gamma-elemene, ethyl decdienoate, ethyl maltol, ethyl propionate, ethylvanillin, eucalyptol, alpha-eudesmol, beta-eudesmol, gamma-eudesmol, eugenol, cis-beta-famesene, trans-gamma bisabolene, fenchone, fenchol, geraniol, alpha-guaiene, guaiol, methyl anthranilate, methyl salicylate, 2-methyl-4-heptanone, 3-methyl-4-heptanone, hexyl acetate, ipsdienol, isoamyl acetate, lemenol, limonene, d-limonene, linolool, alpha-longipinene, menthol, gamma-muurolene, myrcene, nerolidol, trans-nerolidol, nerol, beta-ocimene, octyl acetate, alpha-phellandrene, phytol, alpha-pinene, beta-pinene, pulegone, sabinene, cis-sabinene hydrate, beta-selinene, alpha-selinene, gamma-terpinene, terpinolene, terpineol, terpineol-4-ol, alpha-terpinene, alpha-thujene, vanillin, viridiflorene, and alpha-ylange.

3. The chewing gum of claim 2, wherein said chewing gum consists essentially of at least 0.1% each in the total oral delivery vehicle of two of said terpenoids.

4. The chewing gum of claim 2, wherein said chewing gum consists essentially of at least 0.1% each in the total oral delivery vehicle of three of said terpenoids.

5. The chewing gum of claim 1, wherein said chewing gum is substantially free of tetrahydrocannabinol.

6. The chewing gum of claim 1, wherein said chewing gum consists essentially of at least 2% w/w each of isolated cannabigerolic acid, isolated cannabichromenic acid and isolated cannabinol.

7. The chewing gum of claim 1, wherein said chewing gum consists essentially of at least 5% w/w each of isolated cannabigerolic acid, isolated cannabichromenic acid and isolated cannabinol.

8. The chewing gum of claim 1, wherein said chewing gum consists essentially of at least 10% w/w each of isolated cannabigerolic acid, isolated cannabichromenic acid and isolated cannabinol.

9. A polymeric thin film consisting essentially of at least 1% w/w each of at least two isolated cannabinoids selected from the group consisting of isolated cannabigerolic acid, isolated cannabichromenic acid and isolated cannabinol in a polymeric thin film, wherein the base compound is selected from the group consisting of hydroxy propyl methyl cellulose, hydroxy propyl cellulose, starch, pullulan, pectin, and gelatin.

10. The polymeric thin film of claim 9, wherein said polymeric thin film consists essentially of at least 1% w/w each of Cannabigerolic acid A (Z)-CBGA-$C_5$ A, Cannabichromenic acid A CBCA-$C_5$ A, and Cannabinol CBN-$C_5$.

11. The polymeric thin film of claim 9, further consisting essentially of at least 0.1% w/w each in the polymeric thin film of at least one terpenoid selected from the group consisting of Alloaromadendrene, allyl hexanoate, benzaldehyde, (Z)-a-cis-bergamotene, (Z)-a-trans-bergamotene, beta-bisabolol, epi-alpha-bisabolol, beta-bisabolene, borneol, c-gamma-bisabolene, borneol acetate, alpha-cadinene, camphene, camphor, cis-carveol, caryophyllene, alpha-humulene, gamma-cadinene, delta-3-carene, caryophyllene oxide, 1,8-cineole, citral A, citral B, cinnameldehyde, alpha-copaene, gamma-curcumene, beta-cymene, beta-elemene, gamma-elemene, ethyl decdienoate, ethyl maltol, ethyl propionate, ethylvanillin, eucalyptol, alpha-eudesmol, beta-eudesmol, gamma-eudesmol, eugenol, cis-beta-famesene, trans-gamma bisabolene, fenchone, fenchol, geraniol, alpha-guaiene, guaiol, methyl anthranilate, methyl salicylate, 2-methyl-4-heptanone, 3-methyl-4-heptanone, hexyl acetate, ipsdienol, isoamyl acetate, lemenol, limonene, d-limonene, linolool, alpha-longipinene, menthol, gamma-muurolene, myrcene, nerolidol, trans-nerolidol, nerol, beta-ocimene, octyl acetate, alpha-phellandrene, phytol, alpha-pinene, beta-pinene, pulegone, sabinene, cis-sabinene hydrate, beta-selinene, alpha-selinene, gamma-terpinene, terpinolene, terpineol, terpineol-4-ol, alpha-terpinene, alpha-thujene, vanillin, viridiflorene, and alpha-ylange.

12. The polymeric thin film of claim 11, wherein said polymeric thin film consists essentially of at least 0.1% each in the total oral delivery vehicle of two of said terpenoids.

13. The polymeric thin film of claim 11, wherein said polymeric thin film consists essentially of at least 0.1% each in the total oral delivery vehicle of three of said terpenoids.

14. The polymeric thin film of claim 9, wherein said polymeric thin film is substantially free of tetrahydrocannabinol.

15. The polymeric thin film of claim 9, wherein said polymeric thin film consists essentially of at least 2% w/w each of isolated cannabigerolic acid, isolated cannabichromenic acid and isolated cannabinol.

16. The polymeric thin film of claim 9, wherein said polymeric thin film consists essentially of at least 5% w/w each of isolated cannabigerolic acid, isolated cannabichromenic acid and isolated cannabinol.

17. The polymeric thin film of claim 9, wherein said polymeric thin film consists essentially of at least 10% w/w each of isolated cannabigerolic acid, isolated cannabichromenic acid and isolated cannabinol.

* * * * *